United States Patent
Moore

(10) Patent No.: US 9,605,267 B2
(45) Date of Patent: Mar. 28, 2017

(54) COMPOSITIONS AND METHODS FOR GENETIC CONSTRUCTS

(71) Applicant: UNIVERSITY OF CENTRAL FLORIDA RESEARCH FOUNDATION, INC., Orlando, FL (US)

(72) Inventor: Sean Moore, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 27 days.

(21) Appl. No.: 14/419,215

(22) PCT Filed: Aug. 2, 2013

(86) PCT No.: PCT/US2013/053486
§ 371 (c)(1),
(2) Date: Feb. 2, 2015

(87) PCT Pub. No.: WO2014/022805
PCT Pub. Date: Feb. 6, 2014

(65) Prior Publication Data
US 2015/0299714 A1    Oct. 22, 2015

Related U.S. Application Data

(60) Provisional application No. 61/679,012, filed on Aug. 2, 2012.

(51) Int. Cl.
*C12N 15/63* (2006.01)
*C12N 15/52* (2006.01)
*C12N 15/65* (2006.01)

(52) U.S. Cl.
CPC ............ *C12N 15/63* (2013.01); *C12N 15/52* (2013.01); *C12N 15/635* (2013.01); *C12N 15/65* (2013.01); *C12N 2999/005* (2013.01)

(58) Field of Classification Search
None
See application file for complete search history.

(56) References Cited

U.S. PATENT DOCUMENTS

| 6,720,142 | B1 | 4/2004 | Hall |
| 7,871,604 | B1 | 1/2011 | Curtiss |
| 2002/0061579 | A1 | 5/2002 | Farrand |
| 2005/0118719 | A1 | 6/2005 | Schmidt |
| 2008/0115233 | A1 | 5/2008 | Alphey |
| 2011/0020399 | A1 | 1/2011 | Santiago |

FOREIGN PATENT DOCUMENTS

| CA | 2880819 | 2/2014 |
| CN | 101608170 | 6/2011 |
| EP | 2880166 | 6/2015 |
| WO | WO 01/46403 | 6/2001 |
| WO | WO 2014/022805 | 2/2014 |

OTHER PUBLICATIONS

Stegmeier et al. A lentiviral microRNA-based system for single-copy polymerase II-regulated RNA interference in mammalian cells. 13212-13217_PNAS_Sep. 13, 2005_vol. 102_No. 37.*
http://www.addgene.org/browse/sequence/7008/giraffe-analyze/. 2005.*
International Search Report and Written Opinion dated Jan. 22, 2014 for International Application No. PCT/US2013/053486 (Inventor—Sean Moore // Applicant—University of Central Florida Research Foundation, Inc.) (12 pages).
International Preliminary Report on Patentability dated Feb. 3, 2015 for International Application No. PCT/US2013/053486 (Inventor—Sean Moore // Applicant—University of Central Florida Research Foundation, Inc.) (9 pages).
U.S. Appl. No. 61/679,012, filed Aug. 2, 2012, Moore.
Communication Pursuant to Rules 161(2) and 162 EPC dated Apr. 1, 2015 for European Application No. EP 13825974.2 (Inventor—Sean Moore // Applicant—University of Central Florida Research Foundation, Inc.) (2 pages).
Response to Communication Pursuant to Rules 161(2) and 162 EPC dated Oct. 12, 2015 for European Application No. 13825974.2 (Inventor—Sean Moore // Applicant—University of Central Florida Research Foundation, Inc.) (3 pages).
Extended European Search Report dated Mar. 18, 2016 for European Application No. 13825974.2 (Inventor—Sean Moore // Applicant—University of Central Florida Research Foundation, Inc.) (13 pages).
Bender A, et al. (1991) Use of a screen for synthetic lethal and multicopy suppressee mutants to identify two new genes involved in morphogenesis in *Saccharomyces cerevisiae*. Mol Cell Biol. 11(3):1295-1305.
Bernhardt TG, et al. (2004) Screening for synthetic lethal mutants in *Escherichia coli* and identification of EnvC (YibP) as a periplasmic septal ring factor with murein hydrolase activity. Mol Microbiol. 52(5):1255-1669.
Ferrández A, et al. (1997) Genetic characterization and expression in heterologous hosts of the 3-(3-hydroxyphenyl)propionate catabolic pathway of *Escherichia coli* K-12. J Bacteriol. 179(8):2573-2581.
Lobo I. (2008) Mendelian Ratios and Lethal Genes. Nature Education. 1:1.
Prival MJ, et al. (1998) Chemicals mutagenic in *Salmonella typhimurium* strain TA1535 but not in TA100. Mutat Res. 412(3):251-260.
Schumacher MA. (2008) Structural biology of plasmid partition: uncovering the molecular mechanisms of DNA segregation. Biochem J. 412(1):1-18.
Wu S, et al. (2008) A protocol for constructing gene targeting vectors: generating knockout mice for the cadherin family and beyond. Nat Protoc. 3(6):1056-1076.
Xie Z, et al. (2011) Cloning-independent and counterselectable markerless mutagenesis system in *Streptococcus mutans*. Appl Environ Microbiol. 77(22):8025-8033.
Youngren B, et al. (1997) Altered ParA partition proteins of plasmid P1 act via the partition site to block plasmid propagation. Mol Microbiol. 25(6):1023-1030.

* cited by examiner

*Primary Examiner* — Neil P Hammell
(74) *Attorney, Agent, or Firm* — Akerman LLP

(57) ABSTRACT

In an aspect, the invention relates to compositions and methods for genetic constructs. This abstract is intended as a scanning tool for purposes of searching in the particular art and is not intended to be limiting of the present invention.

6 Claims, 2 Drawing Sheets

COMPOSITIONS AND METHODS FOR GENETIC CONSTRUCTS

CROSS REFERENCE TO RELATED PATENT APPLICATIONS

This application is a National Phase Application of International Application No. PCT/US2013/053486, filed Aug. 2, 2013, which claims the benefit of U.S. Provisional Application No. 61/679,012, filed Aug. 2, 2012. The contents of the prior international and provisional applications are hereby incorporated by reference herein in their entirety.

REFERENCE TO SEQUENCE LISTING

The Sequence Listing submitted May 4, 2015, as a text file named "26150_0033U2_Revised_Sequence_Listing.txt," created on Apr. 3, 2015, and having a size of 28,720 bytes is hereby incorporated by reference pursuant to 37 C.F.R. §1.52(e)(5).

BACKGROUND

Dominant-lethal variants of genes represent a particularly important class of mutants. Dominant lethal variants can be used to reveal the pathways that are directly involved in a gene's function. Dominant lethal variants can be used to identify the important components of a gene's encoded product. Dominant-lethality means that a mutant gene kills (or impedes) a cellular function or metabolism. Thus, identifying genes with this trait is difficult because cells harboring a dominant-lethal gene form are typically not recovered. Currently, the screening for dominant-lethal forms of genes is performed by replica-plating massive libraries of mutants under inducing and non-inducing conditions. The current screening methods are laborious, expensive, and time-consuming.

Despite advances in screening for dominant-lethal forms of genes, there is still a need for methods that are efficient in terms of both time and resources. These needs and other needs are satisfied by the present invention.

BRIEF SUMMARY

The present invention comprises methods and compositions comprising a DNA construct to be integrated into a genome and an active-replication instable DNA construct.

Disclosed herein is a method for identifying a dominant lethal gene in a cell, comprising stably integrating into the genome of a cell a DNA construct comprising a reporter gene under the control of a first sequence of a pair of promoter sequences, a reporter gene for determining incorporation of the DNA construct in the genome, and a copy of a query gene under the control of the second sequence of the pair of promoter sequences, wherein the pair of promoter sequences is under the control of a repressor protein; introducing into the cell a par⁻ plasmid comprising a genetic sequence encoding the repressor protein, a reporter gene for determining the presence of the plasmid in the cell, and a selectable marker for plasmid selection; creating a mutant library by mutagenesis; and screening the mutant library for progeny cells, wherein replicate cells are healthy when the repressor is present, and wherein replicate cells are toxic when the repressor is absent, thus identifying a dominant lethal gene.

Disclosed herein is a method for identifying a second site of suppression for a variant gene, comprising introducing into a cell a par⁻ plasmid comprising a genetic sequence encoding a repressor protein, a reporter gene for determining the presence of the plasmid in the cell, and a selectable marker for plasmid selection; stably integrating into the genome of the cell a DNA construct comprising a reporter gene under the control of a first sequence of a pair of promoter sequences, a reporter gene for detecting incorporation of the DNA construct in the genome, and a copy of a variant query gene under the control of the second sequence of the pair of promoter sequences, wherein the pair of promoter sequences is under the control of the repressor protein; serially culturing the cells; and selecting for cells that are healthy in the absence of the plasmid. Disclosed herein is a method for screening for compounds that inhibit distinct gene variants, comprising introducing into a cell a par⁻ plasmid comprising a genetic sequence encoding a repressor protein, a reporter gene for determining the presence of the plasmid in the cell, and a selectable marker for plasmid selection; stably integrating into the genome of the cell a DNA construct comprising a reporter gene under the control of a first sequence of a pair of promoter sequences, a reporter gene for detecting incorporation of the DNA construct in the genome, and a copy of a variant query gene under the control of the second sequence of the pair of promoter sequences, wherein the pair of promoter sequences is under the control of the repressor protein, and culturing cells in the presence of a compound, wherein the cells reproduce when the compound is an inhibitor of the variant gene product and the repressor is present.

Disclosed herein is a method for identifying cells that cannot tolerate a gene variant, comprising introducing into a cell a par⁻ plasmid comprising a genetic sequence encoding a repressor protein, a reporter gene for determining the presence of the plasmid in the cell, and a selectable marker for plasmid selection; stably integrating into the genome of the cell a DNA construct comprising a reporter gene under the control of a first sequence of a pair of promoter sequences, a reporter gene for detecting incorporation of the DNA construct in the genome, and a copy of a variant query gene under the control of the second sequence of the pair of promoter sequences, wherein the pair of promoter sequences is under the control of the repressor protein; and selecting cells that reproduce in the presence of the repressor.

Disclosed herein is a composition comprising a DNA construct comprising SEQ ID NO: 1.

Disclosed herein is a composition comprising a DNA construct comprising SEQ ID NO:2.

Disclosed herein is a composition comprising a DNA construct comprising a modified version of SEQ ID NO: 1. Disclosed herein is a composition comprising a DNA construct comprising a modified version of SEQ ID NO:2. Disclosed herein is a composition comprising a first DNA construct comprising a SEQ ID NO:1 or SEQ ID NO:2, and optionally, a query gene, and a second DNA construct comprising at least a sequence encoding a repressor protein that interacts with the first DNA construct to repress expression of at least a query gene, for example, SEQ ID NO:1 or SEQ ID NO:2, or a modified version of SEQ ID NO:1 or SEQ ID NO:2.

Disclosed herein is a DNA construct comprising SEQ ID NO:1. Disclosed herein is a DNA construct comprising SEQ ID NO:2. Disclosed herein is a DNA construct comprising a modified version of SEQ ID NO:1. Disclosed herein is a DNA construct comprising a modified version of SEQ ID NO:2. Disclosed herein is a DNA construct comprising at least a sequence encoding a repressor protein that interacts with a separate DNA construct to repress expression of a query gene present in the separate DNA construct.

Disclosed herein is a DNA construct comprising SEQ ID NO:2, wherein the PheS open reading frame is replaced with the open reading frame of a query gene. Disclosed herein is a DNA construct comprising SEQ ID NO:2, wherein the nucleotides at positions 4369 through 5352 are replaced with a query gene, i.e., a modified version of SEQ ID NO:2.

Disclosed herein is an isolated nucleic acid molecule comprising SEQ ID NO:1. Disclosed herein is an isolated nucleic acid molecule comprising SEQ ID NO:2. Disclosed herein is an isolated nucleic acid molecule comprising a modified version of SEQ ID NO:1. Disclosed herein is an isolated nucleic acid molecule comprising a modified version of SEQ ID NO:2.

Disclosed herein is an isolated nucleic acids molecule comprising a second DNA construct comprising at least a sequence encoding a repressor protein that interacts with the first DNA construct to repress expression of at least a query gene.

Disclosed herein is a cell comprising one or more of the disclosed constructs.

Disclosed herein is a kit comprising at least a DNA construct comprising SEQ ID NO: 1.

Disclosed herein is a kit comprising at least a DNA construct comprising SEQ ID NO:2.

Disclosed herein is a kit comprising at least a DNA construct comprising a modified version of SEQ ID NO:1. Disclosed herein is a kit comprising at least a DNA construct comprising a modified version of SEQ ID NO:2. Disclosed herein is a kit comprising at least a DNA construct comprising SEQ ID NO:1 and SEQ ID NO:2. Disclosed herein is a kit comprising at least a DNA construct comprising a modified version of SEQ ID NO:1 and a modified version of SEQ ID NO:2. A kit may optionally comprise cells.

Disclosed herein is a kit comprising at least a DNA construct comprising SEQ ID NO:2, and optionally cells and instructions for replacing PheS in the DNA construct with a query gene open reading frame or ORF. Disclosed herein is kit comprising a first DNA construct comprising a SEQ ID NO:1 or SEQ ID NO:2, or a modified version of SEQ ID NO:1 or modified version of SEQ ID NO:2, and optionally, a query gene.

Disclosed herein is a kit comprising cells comprising a stably integrated DNA construct and a par⁻ plasmid, wherein the DNA construct comprises a reporter gene under the control of a first sequence of a pair of promoter sequences, a reporter gene for detecting incorporation of the DNA construct in the genome, and a copy of a query gene under the control of the second sequence of the pair of promoter sequences, and wherein the par⁻ plasmid comprises a genetic sequence encoding a repressor protein, a reporter gene for determining the presence of the plasmid in the cell, and a selectable marker for plasmid selection.

BRIEF DESCRIPTION OF THE FIGURES

The accompanying figures, which are incorporated in and constitute a part of this specification, illustrate several aspects and together with the description serve to explain the principles of the invention.

Figure 1:
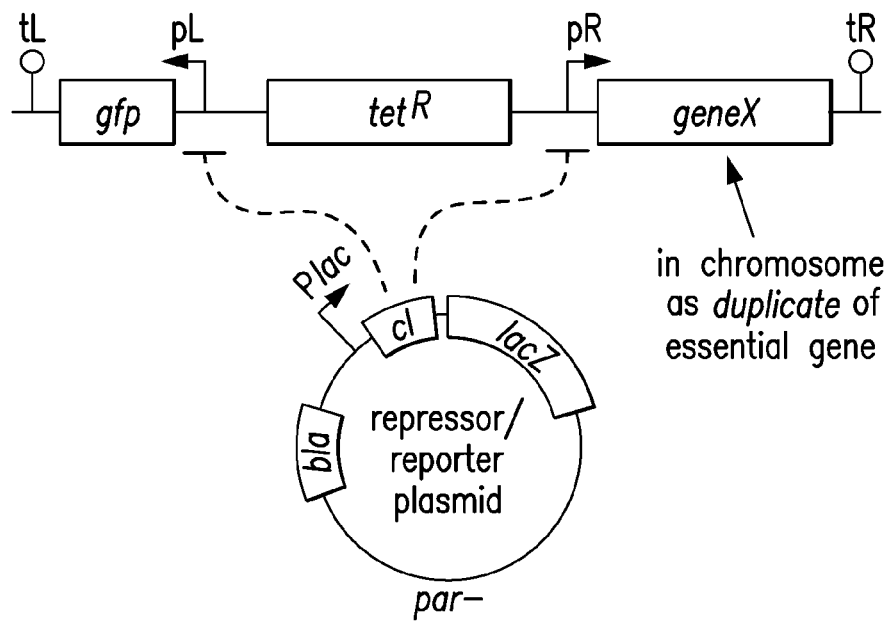
FIG. 1 is a schematic of a dominant-lethal screening system.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

A genetic system called a "synthetic-lethal screen" was developed by yeast biologists and later adapted for use in *E. coli*. In a synthetic-lethal screen, a non-essential gene of interest is moved from the chromosome onto an unstable plasmid containing a reporter. When the plasmid is lost during cell division, so is the reporter, and the colonies become sectored in appearance. Random mutagenesis is then applied to a culture containing the reporter plasmid and colonies are screened for those that cannot grow well in the absence of the plasmid (the colonies retain the color of the reporter). In effect, mutants are sought that render the non-essential gene essential. Mapping of the mutations reveals redundant pathways and other important players related to the function of the query gene.

Unlike a plasmid-based expression system, the disclosed compositions and methods comprise a single copy of the gene of interest (or query gene) that is stably integrated in the chromosome. Thus, expression of the gene of interest is uniform. Additionally, one mutagenic process creates a mutant library that is simultaneously screened for both intragenic and intergenic dominant-lethality.

Thus, the compositions and methods described herein provide for the design and implementation of a genetic system that allows for: (1) identification of a dominant-lethal or dominant-toxic form of a gene (including essential genes), (2) the screening of compounds that inhibit distinct versions of gene products, and (3) the identification of mutant cells that cannot tolerate the expression of a gene variant that may be otherwise harmless. Furthermore, the compositions and methods disclosed herein allow for the interrogation of non-phenotypic mutants of genes of interest. For example, a situation is often encountered in which changing conserved regions on essential genes leads to no overt phenotype, despite the fact that a conserved pathway has been interrupted. Mutant cells that do not tolerate the expression of the altered gene can be recovered. Moreover, the recovery of these genes can reveal the other genes in the involved pathway.

Disclosed herein is a genetic system that allows, for the first time, synthetic-lethal screening using essential genes in *E. coli*. Unlike a plasmid-based expression system, the disclosed system comprises a single copy of the query gene (i.e., gene of interest) that is stably integrated in the chromosome. A wild-type copy of the gene exists elsewhere in the genome. Thus, expression of the gene of interest is uniform. Additionally, one mutagenic process creates a mutant library that is simultaneously screened for both intragenic and intergenic dominant-lethality. The library can also be screened for reversions. Thus, the disclosed system can also be used to identify additional genes that interact with particular regions of a gene of interest. The recovery of dominant-lethal forms of essential genes that may then be used for identifying interacting partners, screening for second-site suppressors, or for controllably inhibiting critical pathways. Compounds that selectively interfere with a particular form of a query gene while not interfering with another form can also be identified.

In addition to being used to identify classical dominant-lethal forms of a gene, if the interrogated copy of the gene in the disclosed genetic control system is a non-phenotypic mutant (e.g., with highly-conserved surface residues mutated), then the mutations that cause dominant-lethality can be in other genes specifically related to the function of the conserved residues. Thus, the function of important regions of a gene can be elucidated by determining the systems that, when mutated, force the cell to require only the wild-type version of the interrogated gene.

A. METHODS

1. Methods for Identifying a Dominant Lethal Gene

Disclosed herein is a method for identifying a dominant lethal gene in a cell. In an aspect, the method can comprise identifying one or more dominant lethal genes. In an aspect, the method for identifying a dominant lethal gene in a cell can comprise (a) stably integrating into the genome of a cell a DNA construct comprising a reporter gene under the control of a first sequence of a pair of promoter sequences, a reporter gene for determining incorporation of the DNA construct in the genome, and a copy of a query gene under the control of the second sequence of the pair of promoter sequences, wherein the pair of promoter sequences is under the control of a repressor protein; (b) introducing into the cell a par⁻ plasmid comprising a genetic sequence encoding the repressor protein, a reporter gene for determining the presence of the plasmid in the cell, and a selectable marker for plasmid selection; (c) creating a mutant library by mutagenesis; and (d) screening the mutant library for progeny cells, wherein replicate cells are healthy when the repressor is present, and wherein replicate cells are toxic when the repressor is absent, thus identifying a dominant lethal gene. In an aspect, the method further comprises sequencing the cells.

In an aspect, the disclosed cells can be *E. coli* cells. In an aspect, a par⁻ plasmid can be unstable in that it exhibits defective partitioning. In an aspect, mutagenesis can comprise contact or exposure to one or more mutagenic substances. In an aspect, mutagenesis can be due to contact with N-ethyl-N-nitrosourea. In an aspect, mutagenesis can be due to exposure to ultraviolet radiation.

In an aspect, the pair of promoter sequences can comprise Lambda pR promoter and Lambda pL promoter. In an aspect, the repressor protein can be Lambda repressor (cI). In an aspect, the wild-type query genome can also be found in the genome.

2. Methods for Identifying a Second Site of Suppression

Disclosed herein is a method for identifying a second site of suppression. In an aspect, the method can comprise identifying one or more second sites of suppression. In an aspect, a method for identifying a second site of suppression for a variant gene can comprise (a) introducing into a cell a par⁻ plasmid comprising a genetic sequence encoding a repressor protein, a reporter gene for determining the presence of the plasmid in the cell, and a selectable marker for plasmid selection; (b) stably integrating into the genome of the cell a DNA construct comprising a reporter gene under the control of a first sequence of a pair of promoter sequences, a reporter gene for detecting incorporation of the DNA construct in the genome, and a copy of a variant query gene under the control of the second sequence of the pair of promoter sequences, wherein the pair of promoter sequences is under the control of the repressor protein; (c) serially culturing the cells; and (d) selecting for cells that are healthy in the absence of the plasmid. In an aspect, the method can further comprise sequencing the cells.

In an aspect, the disclosed cells can be *E. coli* cells. In an aspect, a par⁻ plasmid can be unstable in that it exhibits defective partitioning.

In an aspect, the disclosed one or more second sites of suppression can be intragenic. In an aspect, the disclosed one or more second sites of suppression can be intergenic. In an aspect, the disclosed one or more second sites of suppression can be reversions.

In an aspect, the pair of promoter sequences can comprise Lambda pR promoter and Lambda pL promoter. In an aspect, the repressor protein can be Lambda repressor (cI). In an aspect, the wild-type query genome can also be found in the genome.

3. Methods for Screening for Compounds that Inhibit Distinct Gene Variants

Disclosed herein is a method for screening for inhibitory compounds. In an aspect, the method can comprise identifying one or more inhibitor compounds for one or more distinct gene variants. In an aspect, a method for screening for compounds that inhibit distinct gene variants comprises (a) introducing into a cell a par⁻ plasmid comprising a genetic sequence encoding a repressor protein, a reporter gene for determining the presence of the plasmid in the cell, and a selectable marker for plasmid selection; (b) stably integrating into the genome of the cell a DNA construct comprising a reporter gene under the control of a first sequence of a pair of promoter sequences, a reporter gene for detecting incorporation of the DNA construct in the genome, and a copy of a variant query gene under the control of the second sequence of the pair of promoter sequences, wherein the pair of promoter sequences is under the control of the repressor protein, and culturing cells in the presence of a compound, wherein the cells reproduce when the compound is an inhibitor of the variant gene product and the repressor is present. In an aspect, the method can further comprise sequencing the cells.

In an aspect, the disclosed cells can be *E. coli* cells. In an aspect, a par⁻ plasmid can be unstable in that it exhibits defective partitioning.

In an aspect, the pair of promoter sequences can comprise Lambda pR promoter and Lambda pL promoter. In an aspect, the repressor protein can be Lambda repressor (cI). In an aspect, the wild-type query genome can also be found in the genome.

4. Methods for Identifying Cells that Cannot Tolerate a Gene Variant

Disclosed herein is a method identifying cells that cannot tolerate a gene variant. In an aspect, a method for identifying cells that cannot tolerate a gene variant can comprise (a) introducing into a cell a par– plasmid comprising a genetic sequence encoding a repressor protein, a reporter gene for determining the presence of the plasmid in the cell, and a selectable marker for plasmid selection; (b) stably integrating into the genome of the cell a DNA construct comprising a reporter gene under the control of a first sequence of a pair of promoter sequences, a reporter gene for detecting incorporation of the DNA construct in the genome, and a copy of a variant query gene under the control of the second sequence of the pair of promoter sequences, wherein the pair of promoter sequences is under the control of the repressor protein; and (c) selecting cells that reproduce in the presence of the repressor. In an aspect, the method can further comprise sequencing the cells.

In an aspect, the disclosed cells can be *E. coli* cells. In an aspect, a par⁻ plasmid can be unstable in that it exhibits defective partitioning.

In an aspect, the pair of promoter sequences can comprise Lambda pR promoter and Lambda pL promoter. In an aspect, the repressor protein can be Lambda repressor (cI). In an aspect, the wild-type query genome can also be found in the genome.

B. COMPOSITIONS

Disclosed herein are compositions used in methods for identifying a dominant lethal gene.

Disclosed herein are compositions used in methods for identifying a second site of suppression.

Disclosed herein are compositions used in methods for screening for compounds that inhibit distinct gene variants. Disclosed herein are compositions used in method for identifying cells that cannot tolerate a gene variant. In an aspect, a disclosed composition comprises a DNA construct, a nucleic acid molecule, a cell, and/or a kit.

In an aspect, SEQ ID NO:1 comprises ds-DNA comprising 13387 bp. In an aspect, SEQ ID NO:1 is caattcggga caccatcgaa tggtgcaaaa cctttcgcgg tatggcatga tagcgcccgg aagagagtca attcagggtg gtgaatgtga aaccagtaac gttatacgat gtcgcagagt atgccggtgt ctcttatcag accgtttccc gcgtggtgaa ccaggccagc cacgttctg cgaaaacgcg ggaaaaagtg gaagcggcga tggcggagct gaattacatt cccaaccgcg tggcacaaca actggcgggc aaacagtcgt tgctgattgg cgttgccacc tccagtctgg ccctgcacgc gccgtcgcaa attgtcgcgg cgattaaatc tcgcgccgat caactgggtg cca gcgtggt ggtgtcgatg gtagaacgaa gcggcgtcga agcctgtaaa gcg gcggtgc acaatctctct cgcgcaacgc gtcagtgggc tgatcattaa ctatccgctg gatgaccagg atgccattgc tgtggaagct gcctgcacta atgttccggc gttatttctt gatgtctctg accagacacc catcaacagt attatttct cccatgaaga cggtacgcga ctgggcgtgg agcatctggt cgcattgggt caccagcaaa tcgcgctgtt agcgggccca ttaagttctg tctcgcgcg tctgcgtctg gctggctggc ataaatatct cactcgcaat caaattcagc cgatagcgga acgggaaggc gactggagtg ccatgtccgg ttttcaacaa accatgcaaa tgctgaatga gggcatcgtt cccactgcga tgctggttgc caacgatcag atggcgctgg gcgcaatgcg cgccattacc gagtccggc tgcgcgttgg tgcggatatc tcggtagtgg gatacgacga taccgaagac agctcatgtt atatcccgcc gtcaaccacc atcaaacagg attttcgcct gctggggcaa accagcgtgg accgcttgct gcaactctct caggcgcagg cggtgaaggg caatcagctg ttgcccgtct cactggtgaa aagaaaaacc accctggcgc ccaatacgca aaccgcctct cccgcgcgt tggccgattc attaatgcag ctggcacgac aggtttcccg actggaaagc gggcagtgag cgcaacgcaa ttaatgtgag ttagctcact cattaggcac cccaggcttt acactttat cttccggctc gtatgttgtg tggaattgtg agcggataac aatttcacac aggaggtacc ttatgagcac aaaaaagaaa ccattaacac aagagcagct tgaggacgca cgtcgcctta agcaattta tgaaaaaaag aaaatgaac ttggcttatc ccaggaatct gtcgcagaca agatggggat ggggcagtca ggcgttggtg ctttatttaa tggcatcaat gcattaaatg cttataacgc cgcattgctt gcaaaaattc tcaaagttag cgttgaagaa tttagcc ctt caatcgccag agaaatctac gagatgtatg aagcggttag tatgcagccg tcacttagaa gtgagtatga gtacccgtgt ttttctcatg ttcaggcagg gatgt tctca cctgagctta gaaccttac caaaggtgat gcggagagat gggtaagcac aaccaaaaaa gccagtgatt ctgcattctg gcttgaggtt gaagg taatt ccatgaccgc accaacaggc tccaagccaa gcttcctga cggaatgtta attctcgttg accctgagca ggctgttgag ccaggtgatt tctgcatagc cagacttggg ggtgatgagt ttaccttcaa gaaactgatc agggatagcg gtcaggtgtt tttacaacca ctaaacccac agtacccaat gatcccatgc aat gagagtt gttccgttgt ggggaaagtt atcgctagtc agtggcctga aga gacgttt ggctaacggc cgaggagata gcttattgat tcactgcccg tcgttt taca acgtcgtgac tgggaaaacc ctggcgttac ccaacttaat cgccttgcag cacatcccc tttcgccagc tggcgtaata gcgaagaggc ccgcaccgat cgcccttccc aacagttgcg cagcctgaat ggcgaatggc gctttgcctg gtttccggca ccagaagcgg tgccggaaag ctggctggag tgcgatcttc ctgaggccga tactgtcgtc gtcccctcaa actggcagat gcacggttac gat gcgccca tctacaccaa cgtaacctat cccattacgg tcaatccgcc gtttgt tccc acggagaatc cgacggggttg ttactcgctc acatttaatg ttgatgaaag ctggctacag gaaggccaga cgcgaattat ttttgatggc gttaactcgg cgtttcatct gtggtgcaac gggcgctggg tcggttacgg ccaggacagt cgtttgccgt ctgaatttga cctgagcgca ttttacgcg ccggagaaaa ccgc ctcgcg gtgatggtgc tgcgttggag tgacggcagt tatctggaag atcag gatat gtggcggatg agcggcattt tccgtgacgt ctcgttgctg cataaaccga ctacacaaat cagcgatttc catgttgcca ctcgcttaa tgatgatttc agc cgcgctg tactggaggc tgaagttcag atgtgcggcg agttgcgtga ctac ctacgg gtaacagttt ctttatggca gggtgaaacg caggtcgcca gcggcac cgc gcctttcggc ggtgaaatta tcgatgagcg tggtggttat gccgatcgcg tcacactacg tctcaacgtc gaaaacccga aactgtggag cgccgaaatc ccgaatctct atcgtgcggt ggttgaactg cacaccggcg acggcacgct gat tgaagca gaagcctgcg atgtcggttt ccgcgaggtg cggattgaaa atg gtctgct gctgctgaac ggcaagccgt tgctgattcg aggcgttaac cgtcac gagc atcatcctct gcatggtcag gtcatggatg agcagacgat ggtgcaggat atcctgctga tgaagcagaa caactttaac gccgtgcgct gttcgcatta tccgaaccat ccgctgtggt acacgctgtg cgaccgctac ggcctgtatg tggtggatga agcaatatatt gaaacccacg gcatggtgcc aatgaatcgt ctgaccgatg atccgcgctg gctaccggcg atgagcgaac gcgtaacgcg aatggtgcag cgcgatcgta atcaccgag tgtgatcatc tggtcgctgg ggaatgaatc aggccacggc gctaatcacg acgcgctgta tcgctggatc aaatctgtcg atccttcccg cccggtgcag tatgaaggcg gcggagccga caccacggcc accgatatta tttgcccgat gtacgcgcgc gtggatgaag accagccctt cccggctgtg ccgaaatggt ccatcaaaaa atggctttcg ctac ctggag agacgcgccc gctgatcctt tgcgaatacg cccacgcgat ggg taacagt cttggcggtt tcgctaaata ctggcaggcg tttcgtcagt atccccgttt acagggcggc ttcgtctggg actgggtgga tcagtcgctg attaaatatg atgaaaacgg caacccgtgg tcggcttacg gcggtgattt tggcgatacg ccgaacgatc gccagttctg tatgaacggt ctggtctttg ccgaccgcac gccgcatcca gcgctgacgg aagcaaaaca ccagcagcag ttttccagt tccgtttatc cgggcaaacc atcgaagtga ccagcgaata cctgttccgt catagcgata acgagctcct gcactggatg gtggcgctgg atggtaagcc gctggcaagc ggtgaagtgc ctctggatgt cgctccacaa ggtaaacagt tgattgaact gcctgaacta ccgcagccgg agagcgccgg gcaactctgg ctcacagtac gcgtagtgca accgaacgcg accgcatggt cagaagccgg gcacatcagc gcctggcagc agtggcgtct ggcggaaaac ctcagtgtga cgctccccgc cgcgtcccac gccatcccgc atctgaccac cagcgaaatg gatttttgca tcgagctggg taataagcgt tggcaattta accgccagtc aggctttctt tcacagatgt ggattggcga taaaaaacaa ctgctgacgc cgct gcgcga tcagttcacc cgtgcaccgc tggataacga cattggcgta agt gaagcga cccgcattga ccctaacgcc tgggtcgaac gctggaaggc ggcgggccat taccaggccg aagcagcgtt gttgcagtgc acggcagata cacttgctga tgcggtgctg attacgaccg ctcacgcgtg gcagcatcag ggg aaaacct tatttatcag ccggaaaacc taccggattg atggtagtgg tcaaatggcg attaccgttg atgttgaagt ggcgagcgat acaccgcatc cggcgcggat tggcctgaac tgccagctgg cgcaggtagc agagcgggta aactggctcg gattagggcc gcaagaaaac tatcccgacc gccttactgc cgcctgtttt gaccgctggg atctgccatt gtcagacatg tatacccgt acgtcttccc gagcgaaaac ggtctgcgct gcgggacgcg cgaattgaat tatgcccac accagtggcg cggcgacttc cagttcaaca tcagccgcta cagtcaacag caactgatgg aaaccagcca tcgccatctg ctgcacgcgg aagaaggcac atggctgaat atcgacggtt tccatatggg gattggtggc gac gactcct ggagcccgtc agtatcggcg gaattacagc tgagcgccgg tcg ctaccat taccagttgg tctggtgtca aaaataataa taaccgggca ggccat gtct gcccgtattt cgcgtaagga aatccattat gtactattta aaaaacacaa actttggat gttcggttta ttctttttct tttactttt tatcatggga gcctacttcc cgtttttccc gatttggcta catgacatca accatatcag caaaagtgat acggg tatta ttttgccgc tatttctctg ttctcgctat tattccaacc gctgtttggt ctgctttctg acaaactcgg gctgcgcaaa tacctgctgt ggattattac cgg catgtta gtgatttg cgccgttctt tattttatc ttcgggccac tgtta caata caacttta gtaggatcga ttgttggtgg tatttatcta ggctttgtt ttaacgccgg tgcgccagca gtagaggcat ttattgagaa agtcagccgt cgcagtaatt tcgaatttgg tcgcgcgcgg atgtttggct gtgttggctg
ggcgctgtgt gcctcgattg tcggcatcat gttcaccatc aataatcagt
ttgttttctg gctgggctct ggctgtgcac tcatcctcgc cgttttactc
tttttcgcca aaacggatgc gccctcttct gccacggttg ccaatgcggt aggt-
gccaac cattcggcat ttagccttaa gctggcactg gaactgttca gacagc-
caaa actgtggttt ttgtcactgt atgttattgg cgtttcctgc acctacgatg
tttttgacca acagtttgct aatttcttta cttcgttctt tgctaccggt gaaca-
gggta cgcgggtatt tggctacgta acgacaatgg gcgaattact taacgc-
ctcg attatgttct ttgcgccact gatcattaat cgcatcggtg ggaaaaacgc
cctgctgctg gctggcacta ttatgtctgt acgtattatt ggctcatcgt tcgc-
cacctc agcgctggaa gtggttattc tgaaaacgct gcatatgttt gaagtaccgt
tcctgctggt gggctgcttt aaatatatta ccagccagtt tgaagtgcgt ttttca-
gcga cgatttatct ggtctgtttc tgcttcttta agcaactggc gatgattttt
atgtctgtac tggcgggcaa tatgtatgaa agcatcggtt tccagggcgc
ttatctggtg ctgggtctgg tggcgctggg cttcaccttta atttccgtgt
tcacgcttag cggccccggc ccgctttccc tgctgcgtcg tcaggtgaat
gaagtcgctt aagcaatcaa tgtcggatgc ggcgcgacgc ttatccgacc
aacatatcat aacggagtga tcgcattgaa catgccaatg accgaaagaa
taagagcagg caagctattt accgatatgt gcgaaggctt accggaaaaa
agactcgtg ggaaaacgtt aatgtatgag tttaatcact cgcatccatc
agaagttgaa aaagagaaa gcctgattaa agaaatgttt gccacggtag
gggaaaacgc ctgggtagaa ccgcctgtct atttctctta cggttccaac atc-
catatag gccgcaattt ttatgcaaat ttcaatttaa ccattgtcga tgactacacg
gtaacaatcg gtgataacgt actgattgca cccaacgtta ctctttccgt
tacgggacac cctgtacacc atgaattgag aaaaaacggc gagatgtact
cttttccgat aacgattgct aataacgtct ggatcggaag tcatgtggtt
attaatccag gcgtcaccat cggggataat tctgttattg gcgcgggtag
tatcgtcaca aaagacattc caccaaacgt cgtggcggct ggcgttcctt
gtcgggttat tcgcgaaata aacgaccggg ataagcacta ttatttcaaa gat-
tataaag ttgaatcgtc agtttaaatt ataaaaattg cctgatacgc tgcgcttatc
aggcctacaa gttcagcgat ctacattagc cgcatccggc atgaacaaag
cgcaggaaca agcgtcgcat catgcctctt tgacccacag ctgcgaaaaa
cgtactggtg caaaacgcag ggttatgatc atcagcccaa cgacgcacag
cgcatgaaat gcccagtcca tcaggtaatt gccgctgata ctacgcagca cgc-
cagaaaaa ccacggggca agcccggcga tgataaaacc gattccctgc
ataaacgcca ccagcttgcc agcaatagcc ggttgcacag agtgatcgag
cgccagcagc aaacagagcg gaaacgcgcc gcccagacct aacccacaca
ccatcgccca caataccggc aattgcatcg cagccagat aaagccgcag
aaccccacca gttgtaacac cagcgccagc attaacagtt tgcgccgatc
ctgatggcga gccatagcag gcatcagcaa agctcctgcg gcttgcccaa
gcgtcatcaa tgccagtaag gaaccgctgt actgcgcgct ggcaccaatc
tcaatataga aagcgggtaa ccaggcaatc aggctggcgt aaccgccgtt
aatcagaccg aagtaaacac ccagcgtcca cgcgcgggga gtgaataccca
cgcgaaccgg agtggttgtt gtcttgtggg aagaggcgac ctcgcgggcg
ctttgccacc accaggcaaa gagcgcaaca acggcaggca gcgccaccag
gcgatgtgtt gataccaggt ttcgctatgt tgaactaacc agggcgttat ggcg-
gcacca agcccaccgc cgccatcag agccgcggac cagccccca tcac-
cagtgg cgtgcgctgc tgaaaccgcc gtttaatcac cgaagcatca ccgcct-
gaat gatgccgatc cccacccccac caagcagtgc gctgctaagc
agcagcgcac tttgcgggta aagctcacgc atcaatgcac cgacggcaat
cagcaacaga ctgatggcga cactgcgacg ttcgctgaca tgctgatgaa
gccagcttcc ggccagcgcc agcccgccca tggtaaccac cggcagagcg
gcccactgcc acggctccta ctgctactcg cgtaacaatc taagtatgt
gccacggact gacgcaatcg ttaaattgac actattgat ggcgtaattt cgac-
catccg tgatacattg aggctgttcc ctggggggtcg ttaccttcca cgag-
caaaac acgtagcccc ttcagagcca gatcctgagc aagatgaaca gaaact-
gagg ttttgtaaac gccacccttta tgggcagcaa ccccgatcac cggtggaaat
acgtcttcag cacgtcgcaa tcgcgtacca aacacatcac gcatatgatt aattt-
gttca attgtataac caacacgttg ctcaaccccgt cctcgaattt ccatatccgg
gtgcggtagt cgccctgctt tctcggcatc tctgatagcc tgagaagaaa
ccccaactaa atccgctgct tcacctattc tccagcgccg ggtatttttc ctcgct-
tccg ggctgtcatc attaaactgt gcaatgcga tagccttcgt catttcatga
ccagcgttta tgcactggtt aagtgtttcc atgagtttca ttctgaacat cctt-
taatca ttgctttgcg ttttttttat aaatcttgca atttactgca aagcaacaac
aaaatcgcaa agtcatcaaa aaaccgcaaa gttgtttaaa ataagagcaa cac-
tacaaaa ggagataaga agagcacata cctcagtcac ttattatcac
tagcgctcgc cgcagccgtg taaccgagca tagcgagcga actggcgagg aagcaaagaa gaactgttct gtcagatagc tcttacgctc agcgcaagaa
gaaatatcca ccgtgggaaa aactccaggt agaggtacac acgcggatag
ccaattcaga gtaataaact gtgataatca accctcatca atgatgacga act-
aaccccc gatatcaggt cacatgacga agggaaagag aaggaaatca act-
gtgacaa actgccctca aatttggctt ccttaaaaat tacagttcaa aaagtat-
gag aaaatccatg caggctgaag gaaacagcaa aactgtgaca aattaccctc
agtaggtcag aacaaatgtg acgaaccacc ctcaaatctg tgacagataa
ccctcgact atcctgtcgt catggaagtg atatcgcgga aggaaaatac
gatatgagtc gtctggcggc ctttctttt ctcaatgtat gagaggcgca ttg-
gagttct gctgttgatc tcattaacac agacctgcag gaagcggcgg
cggaagtcag gcatacgctg gtaactttga ggcagctggt aacgctctat
gatccagtcg attttcagag agacgatgcc tgagccatcc ggcttacgat act-
gacacag ggattcgtat aaacgcatgg catacggatt ggtgatttct tttgttcac
taagccgaaa ctgcgtaaac cggttctgta acccgataaa gaagggaatg
agatatgggt tgatatgtac actgtaaagc cctctggatg gactgtgcgc
acgtttgata aaccaaggaa aagattcata gccttttca tcgccggcat cctct-
tcagg gcgataaaaa accattcct tcccccgcgaa actcttcaat gcctgccgta
tatccttact ggcttccgca gaggtcaatc cgaaatttc agcatattta
gcaacatgga tctcgcagat accgtcatgt tcctgtaggg tgccatcaga
ttttctgatc tggtcaacga acagatacag catacgtttt tgatcccggg aga-
gactata tgccgcctca gtgaggtcgt tgactggac gattcgcggg ctatttt-
tac gttcttgtg attgataacc gctgtttccg ccatgacaga tccatgtgaa
gtgtgacaag ttttagatt gtcacactaa ataaaaaga gtcaataagc
agggataact ttgtgaaaaa acagcttct ctgagggcaa tttgtcacag ggt-
taagggc aatttgtcac agcaggact gtcattgag ggtgatttgt cacact-
gaaa gggcaattc tcacaacacc ttctctagaa ccagcatgga taaggccta
caaggcgctc taaaaagaaa gatctaaaaa ctataaaaa aataattata
aaaatatccc cgtggataag tggataaccc caagggaagt ttttcaggc
atcgtgtgta agcagaatt ataagtgctg ttcctggtc cttcctgct cactc-
gaggg cttcgcctg tcgctcgact gcggcgagca ctactggctg
taaaaggaca gaccacatca tggttctgtg ttcattaggt tgttctgtcc attgct-
gaca taatccgctc cacttcaacg taacaccgca cgaagatttc tattgttcct
gaaggcatat tcaaatcgtt tcgttaccg cttgcaggca tcatgacaga cac-
tacttc ctataaacgc tacacaggct cctgagatta ataatgcgga tctctacgat
aatgggagat tttcccgact gtttcgttcg cttctcagtg ataacagcc agct-
tctctg tttaacagac aaaaacagca tatccactca gttccacatt tccatataaa
ggccaaggca tttattctca ggataattgt ttcagcatcg caaccgcatc
agactccggc atcgcaaact gcaccggtg ccgggcagcc acatccagcg
caaaaacctt cgtgtagact tccgttgaac tgatggactt atgtcccatc
aggctttgca gaactttcag cggtataccg gcatacagca tgtgcatcgc atag-
gaatgg cggaacgtat gtggtgtgac cggaacagag aacgtcacac cgtca-
gcagc agcggcggca accgcctccc caatccaggt cctgaccgtt ctgtc-
cgtca cttcccagat ccgcgctttc tctgtccttc ctgtgcgacg gttacgccgc
tccatgggta ttttcagtgt tgccaccatc gtctgcagct ggctgacgta ccag-
gagtca gagagcggaa ccagccggtg agtctgctga ccggcgggca ttctc-
cccgc cgtcctggca gcttttttcgg tccgttgttt caggtgtcga agtcgcacaa
acggatcgg aggcgcaagc gaaaaattccc cccgcgtcag cgccagtgct
tcattaatgc gtgctccggt gttccacagt gtggccagca gcatcttgcg
gtgcagatcc gggacgtaat ggagcagggc actcacttcc ggagccagca
gatattttgg cagttcatca tggaccatcg acatctggcg aagtgccaga gct-
gccggat aatcaatggc aacaggcagc gatgcaggct gcccggcaga ata-
cactgcc gaggcgtttc cccctggaag ctcccctcgtg cgctctcctg ttccgac-
cct gccgcttacc ggatacctgt ccgccttct cccttcggga agcgtggcgc
tttctcatag ctcacgctgt aggtatctca gttcggtgta ggtcgttcgc
tccaagctgg gctgtgtgca cgaaccccc gttcagcccg accgctgcgc
cttatccggt aactatcgtc ttgagtccaa cccggtaaga cacgacttat cgc-
cactggc agcagccact ggtaacagga ttagcagagc gaggtatgta ggcg-
gtgcta cagagtcctt gaagtggtgg cctaactacg gctacactag aaggaca-
gta tttggtatct gcgctctgct gaagccagtt accttcggaa aaagagttgg
tagctcttga tccggcaaac aaaccaccgc tggtagcggt ggtttttttg-
caagca gcagattacg cgcagaaaaa aaggatctca agaagatcct
ttgatctttt ctacggggtc tgacgctcag tggaacgaaa actcacgtta
agggattttg gtcatgagat tatcaaaaag gatcttacc tagatccttt taaat-
taaaa atgaagtttt aaatcaatct aaagtatata tgagtaaact tggtctgaca
gttaccaatg cttaatcagt gaggcaccta tctcagcgat ctgtctattt cgt-
tcatcca tagttgcctg actccccgtc gtgtagataa ctacgatacg
ggagggctta ccatctggcc ccagtgctgc aatgataccg cgagacccac gctcaccggc tccagattta tcagcaataa accagccagc cggaagggcc gagcgcagaa gtggtcctgc aacttatcc gcctccatcc agtctattaa ttgt- tgccgg gaagctagag taagtagttc gccagttaat agtttgcgca acgttgt- tgc cattgctgca ggcatcgtgt tgtcacgctc gtcgtttggt atggcttcat tcagctccgg ttcccaacga tcaaggcgag ttacatgatc ccccatgttg tgcaaaaaag cggttagctc cttcggtcct ccgatcgttg tcagaagtaa gttg- gccgca gtgttatcac tcatggttat ggcagcactg cataattctc ttactgtcat gccatccgta agatgctttt ctgtgactgg tgagtactca accaagtcat tct- gagaata gtgtatgcgg cgaccgagtt gctcttgccc ggcgtcaaca cggga- taata ccgcgccaca tagcagaact ttaaaagtgc tcatcattgg aaaacgttct tcggggcgaa aactctcaag gatcttaccg ctgttgagat ccagttcgat gtaacccact cgtgcaccca actgatcttc agcatctttt actttcacca gcgtttctgg gtgagcaaaa acaggaaggc aaaatgccgc aaaaaaggga ataagggcga cacggaaatg ttgaatactc atactcttcc ttttcaata ttatt- gaagc atttatcagg gttattgtct catgagcgga tacatatttg aatgtattta gaaaaataaa caaatagggg ttccgcgcac atttccccga aaagtgccac ctgacgtcta agaaaccatt attatcatga cattaaccta taaaaatagg cgtat- cacga ggccctttcg tcttcaa.

In an aspect, SEQ ID NO:2 comprises ds-DNA comprising 6970 bp. In an aspect, SEQ ID NO:2 is tcaaacggca cattcagagt gcgacggaca aaacttgctc caccgtcaca ggctaccagc cactgggctt tgactatttc ccgctgccct tctgccgttt tcaggtgcaa ggt- cacttcg tcatcttgct gactgaaggc ctccagctgc cgggaaaaca agca- gcgcac attcggaaaa cgcgacaccc cttccagcat caccgcatcg acct- gcggct gaataaaggc gttacggcgc ggccagccaa attcatcggt cattgcgctga atatcagcaa aacagcggcc tttcggggtg agaaaaccga tcgcgtgcca cggcgtagtg tgcggcagaa catcatcgac caggccgacc gactgcatgg tgcgcagcgc ctcgtcatca ataccaatcg cacgcgggta gtcgatcaac ttatcgagtt tctccaccac cagcacgtca atgccatct ggc- cgagata gttcgccatc atcagcccaa ccgggccggc accagcgatc gccacctgaa cgctatggtt aacagcaggc tggatgtcag ggtgttgtat tgc- catttca gtacctcacg actcggacaa aatgtcgttg cgcgcacagt acagcg- caac ttattttgtt aaaaacatgt aaatgatttt ttattgtgcg ctcagtatag gaagggtgtt ttcggctaca atcaaaacat gcccgaatgt ggccaggtgt cac- cacgttg ttttaactat agaaatgtca attaatatgc agaacaatga gcagacg- gaa tacaaaaccg tgcgcggctt aacccgcggt ctaatgttat taaatatgtt aaataaactt gatggcggtg ccagcgtcgg gctgctggcg gaactcagcg gcctgcatcg caccactgtg cggcgactgc tggagacgct gcaggaagag ggatatgtcc gccgtagccc ctccgatgat agttttcgac tgaccatcaa agt- gcggcaa ttaagcgaag gatttcgtga cgaacagtgg atttctgcac tggcg- ccccc actgctgggc gatcgttgc gcgaagtggt atggccgaca gatgt- gtcca cgctggatgt tgatgcaatg gtggtacgcg aaaccactca ccgtttcagc cgcttatcct ttcaccgggc aatggtcggg cgacgtttgc cgct- tctgaa aaccgcctcg ggcctgacct ggctggcctt tgcccggaa caagac- cgca aggaattaat cgaaatgtta gcctcccgcc ccggtgatga ctatcaactg gcacgggaac cgttaaagct ggaagccatt ctggcgccgc cgcgcaaaga gggttacgga cagaactacc gcggctggga tcaggaggag aagatcgcct ctatcgcccgt accgctgcgc agtgaacaac gggtgattgg ctgtctgaat ctg- gtgtata tggcgagcgc aatgaccatt gaacaggcag cggaaaagca tcttc- cggcg ctacaacggg tagcaaaaca gatcgaagaa ggggttgaat cgcag- gctat tctggtggcc ggaaggcgaa gcggcatgca tttacgttga caccatcgag cgaactccgg gacgtcagt aatgtgacga tagctgaaaa ctgtacgata aaccaaaaaa tcgtcgggga cattgtaaag gcggcgagcg cggcttttcc cgcgccagcgt gaaagcagtg tggactggcc gtcaggtacc cgtactgtca ccgtgaccga tgaccatcct tttgatcgcc agatagtggt gct- tccgctg acgttcgcg gaagtaagcg tactgtcagc ggcaggacaa cgtat- tcgat gtgttatctg aaagtactga tgaacggtgc ggtgatttat gatggcgcgg cgttagtctg taatcccagc agctgttaca aactcaagaa ggaccatgtg gtcacgcttc tcgttgggat ctttcgaaag ggcagattgt gtggacaggt aatg- gttgtc tggtaaaagg acagggccat cgccaattgg agtatttgt tgatgatggt ctgctagttg aacgcttcca tcttcaatgt tgtgtctaat tttgaagtta actttgattc cattctttg tttgtctgcc atgatgtata cattgtgtga gttatagttg tattccaatt tgtgtccaag aatgttcca tcttctttaa aatcaataccc ttttaactg attctattaa caagggtatc accttcaaac ttgactttag cacgtgtctt gtagttccg tcatctttga aaaatatagt tcttttcctgt acataacctt cgggatggc actctt- gaaa aagtcatgct gtttcatatg atctgggtat ctcgcaaagc attgaacacc ataaccgaaa gtagtgacaa gtgttggcca tggaacaggt agttttccag tagtgcaaat aaatttaagg gtaagtttc cgtatgttgc atcaccttca ccctctccac tgacagaaaa tttgtgccca ttaacatcac catctaattc aacaagaatt ggga- caactc cagtgaaaag ttcttctcct ttacgcatgg tctgtttcct gcgtatcaca caccccaaag ccttctgctt tgaatgctgc ccttcttcag ggcttaattt ttaagagcgt caccttcatg gtggtcagtg cgtcctgctg atgtgctcag tat- caccgcc agtggtattt atgtcaacac cgccagagat aatttatcac cgca- gatggt tatctgtatg ttttttatat gaatttattt tttgcaggggg ggcattgttt ggtaggtgag agatctgaat tgctatgtt agtgagttgt atctatttat ttttcaataa atacaattgg ttatgtgttt tgggggcgat cgtgaggcaa agaaaacccg gcgctgaggc cgggTTaggt cgaggtggcc cggctccatg caccgcgacg caacgcgggg aggcagacaa ggtataggc ggcgcctaca atccatgcca acccgttcca tgtgctcgcc gaggcggcat aaatcgccgt gac- gatcagc ggtccagtga tcgaaggttag gctggtaaga gccgcgagcg atc- cttgaag ctgtccctga tggtcgtcat ctacctgcct ggacagcatg gcctg- caacg cgggcatccc gatgccgccg gaagcgagaa gaatcataat ggggaaggcc atccagcctc gcgtcgcgaa cgccagcaag acgtagccca gcgcgtcggc cgccatgccg gcgataatgc ctgcttctc gccgaaacgt ttg- gtggcgg gaccagtgac gaaggcttga gcgagggcgt gcaagattcc gaataccgca agcgacaggc cgatcatcgt cgccgctccag cgaaagcggt cctgccgaa aatgacccag agcgctgccg gcacctgtcc tacgagttgc atgataaaga agacagtcat aagtgcggcg acgatagtca tgccccgcgc ccaccggaag gagctgactg ggttgaaggc tctcaagggc atcggtcgac gctctccctt atgcgactcc tgcattagga agcagccag tagtaggttg aggc- cgttga gcaccgccgc cgcaaggaat ggtgcatgca aggagatggc gcccaacagt cccccggcca cggggcctgc caccataccc acgccgaaac aagcgctcat gagcccgaag tggcgagccc gatcttcccc atcggtgatg tcggcgatat aggccgccagc aaccgcacct gtgccgccgg tgatgccgac cacgatgcgt ccggcgtaga ggatccacag acgggtgtg tcgccatga tcgcgtagtc gatagtggct ccaagtagcg aagcgagcag gactgggcgg cggccaaagc ggtcggacag tgctccgaga acgggtcgcg ataagaaattg catcaacgca tatagcgcta gcagcacgcc atagtgactg gcgatgctgt cggaatggac gatatcccgc aagaggcccg gcagtaccgg cataaccaag cctatgcta cagcatccag ggtgacggtg ccgaggatga cgatgagcgc attgttagat tcatacacg gtgcctgact gcgttagcaa tttaactgtg ataaac- tacc gcattaaagc ttatcgatga taagctgtca aacatgagaa ttacaactta tatcgtatgg ggctgacttc aggtgcatac gttaaatcta tcaccgcaag gga- taaatat ctaacaccgt gcgtgttgac tattttaccet ctggcggtga taatggttgc atgtactaag gaggttgtat gtcacatctc gcagaactgg ttgccagtgc gaaggcggcc attagccagg cgtcagatgt tgccgcgtta gataatgtgc gcgtcgaata tttgggtaaa aaagggcact taaccttca gatgacgacc ctgcgtgagc tgccgccaga agagcgtccg gcagctggtg cggtatcaa cgaagcgaaa gagcaggttc agcaggcgct gaatgcgcgt aaagcggaac tggaagcgc tgcactgaat gcgcgtctgg cggcgaaac gattgatgtc tctctgccag gtcgtcgcat tgaaaacggc ggtctgcatc cggttacccg tac- catcgac cgtatcgaaa gttcttcgg tgagcttggc tttaccgtgg caac- cgggcc ggaaatcgaa gacgattatc ataacttcga tgctctgaac attcctg- gtc accaccccgc gccgctgac cacgcacactt tctggtttga cactaccgac ctgctgcgta cccagacctc tggcgtacag atccgcacca tgaaagccca gcagccaccg attcgtatca tcgccgcctgg ccgtgtttat cgtaacgact acgaccagac tcacacgccc atgtccatc agatggaagg tctgattgtt gataccaaca tcagcttac caactgaaa ggcacgctgc acgacttcct gcg- taacttc tttgaggaag atttgcagat tcgcttccgt ccttcctact tcccgtttac cgaaccttct tcgagaagtgg acgtcatggg taaaaacggt aaatggctgg aagtgctggg ctgcgggatg gtgcatccga acgtgttgcg taacgttggc atc- gacccgg aagtttactc tggtttcggc ttcgggatgg ggatggagcg tctgac- tatg ttgcgttacg gcgtcaccga cctgcgttca ttcttcgaaa acgatctgcg tttctcaaa cagtttaaat aaggtcttca ggtatcgaa ggtaaggtct ggc- gaacggt gtattaccgg tttgctacca gggaagaacg ggaaggaaag atgag- cacga acctggtttt taaggagtgt cgccagagtg ccgcgatgaa acgggt- attg gcggtatatg gagttaaaag atgaccatct acattactga gctaataaca ggcctgctgg taatcgcagg ccttttatt tgggggagag ggaagtcatg aaaaactaa cctttgaaat tcgatctcca gcacatcagc aaaacgctat tcacgcagta cagcaaatcc ttccagaccc aaccaaacca atcgtagtaa ccattcagga acgcaaccgc agcattataa aaattgcctg atacgctgcg cttatcaggc ctacaagttc agcgatctac attagccgca tccggcatga acaaagcgca ggaacaagcg tcgcatcatg cctctttgac ccacagctgc ggaaaacgta ctggtcaaaa acgcagggtt atgatcatca gcccaacgac gcacagcgca tgaaatgccc agtccatcag gtaattgccg ctgatactac gcagcacgcc agaaaaccac ggggcaagcc cggcgatgat aaaaccgatt ccctgcataa acgccaccag cttgccagca atagccggtt gcacagagtg atcgagcgcc agcagcaaac agagcggaaa cgcgccgccc agacctaacc cacacaccat cgcccacaat accggcaatt gcatcggcag ccagataaag 5
ccgcagaacc ccaccagttg taacaccagc gccagcatta acagtttgcg ccgatcctga tggcgagcca tagcaggcat cagcaaagct cctgcggctt gcccaagcgt catcaatgcc agtaaggaac cgctgtactg cgcgctggca ccaatctcaa tatagaaagc gggtaaccag gcaatcaggc tggcgtaacc gccgttaatc agaccgaagt aaacacccag cgtccacgcg cggggagtga
ataccacgcg aaccggagtg gttgttgtct tgtgggaaga ggcgacctcg cgggcgcttt gccaccacca ggcaaagagc gcaacaacgg caggcagcgc ccaccaggcg agtgtttgat accaggtttc gctatgttga actaaccagg gcgttatggc ggcaccaagc ccaccgccgc ccatcagagc cgcggaccac agccccatca ccagtggcgt gcgctgctga aaccgccgtt taatcaccga aggcat- cacc gcctgaatga tgccgatccc caccccacca agcagtgcgc tgctaagcag cagcgcactt tgcgggtaaa gctcacgcat caatgcaccg acggcaatca gcaacagact gatggcgaca ctgcgacgtt cgctgacatg ctgatgaagc cagcttccgg ccagcgccag cccgcccatg gtaaccaccg gcagagcggt caacagggca gccacgctaa agctcattcc gctcgcctgg
cgcaattgcg gtagcagtgg cccgacggag gtgagcagtg gtcgcatatt aagaccaatc agcaccagta ccagcagcat.

In an aspect, SEQ ID NO:3 represents a sequence excised from SEQ ID NO:2. In an aspect, SEQ ID NO:3 is gtgcgtgttg actatttac ctctggccggt gataatggtt gcatgtacta aggaggttgt atgtca- 25 catc tcgcagaact ggttgccagt gcgaaggcgg ccattagcca ggcgtcagat gttgccgcgt tagataatgt gcgcgtcgaa tatttgggta aaaaagggca cttaacctt cagatgacga ccctgcgtga gctgccgcca gaagagcgtc cggcagctgg tgcggttatc aacgaagcga aagagcaggt tcagcaggcg ctgaatgcgc gtaaagcgga actggaaagc gctgcactga atgcgcgtct
ggcggcggaa acgattgatg tctctctgcc aggtcgtcgc attgaaaacg gcggtctgca tccggttacc cgtaccatcg accgtatcga aagtttcttc ggtgagcttg gctttaccgt ggcaaccggg ccggaaatcg aagacgatta tcataacttc gatgctctga acattcctgg tcaccacccg gcgcgcgctg accacgacac tttctggttt gacactaccc gcctgctgcg taccagacc tctg- 35 gcgtac agatccgcac catgaaagcc cagcagccac cgattcgtat catcgcgcct ggccgtgttt atcgtaacga ctacgaccag actcacacgc cgatgttcca tcagatggaa ggtctgattg ttgataccaa catcagcttt accaacctga aaggcacgct gcacgacttc ctgcgtaact tctttgagga agatttgcag attcgcttcc gtccttccta cttccgttt accgaacctt ctgca- 40 gaagt ggacgtcatg ggtaaaaacg gtaaatggct ggaagtgctg ggctgcggga tggtgcatcc gaacgtgttg cgtaacgttg gcatcgaccc ggaagttac tctggtttcg gcttcgggat ggggatggag cgtctgacta tgttgcgtta cggcgtcacc gacctgcgtt cattcttcga aaacgatctg cgtttcctca aacagtttaa ataa.

1. Constructs and Plasmids

Figure 3:
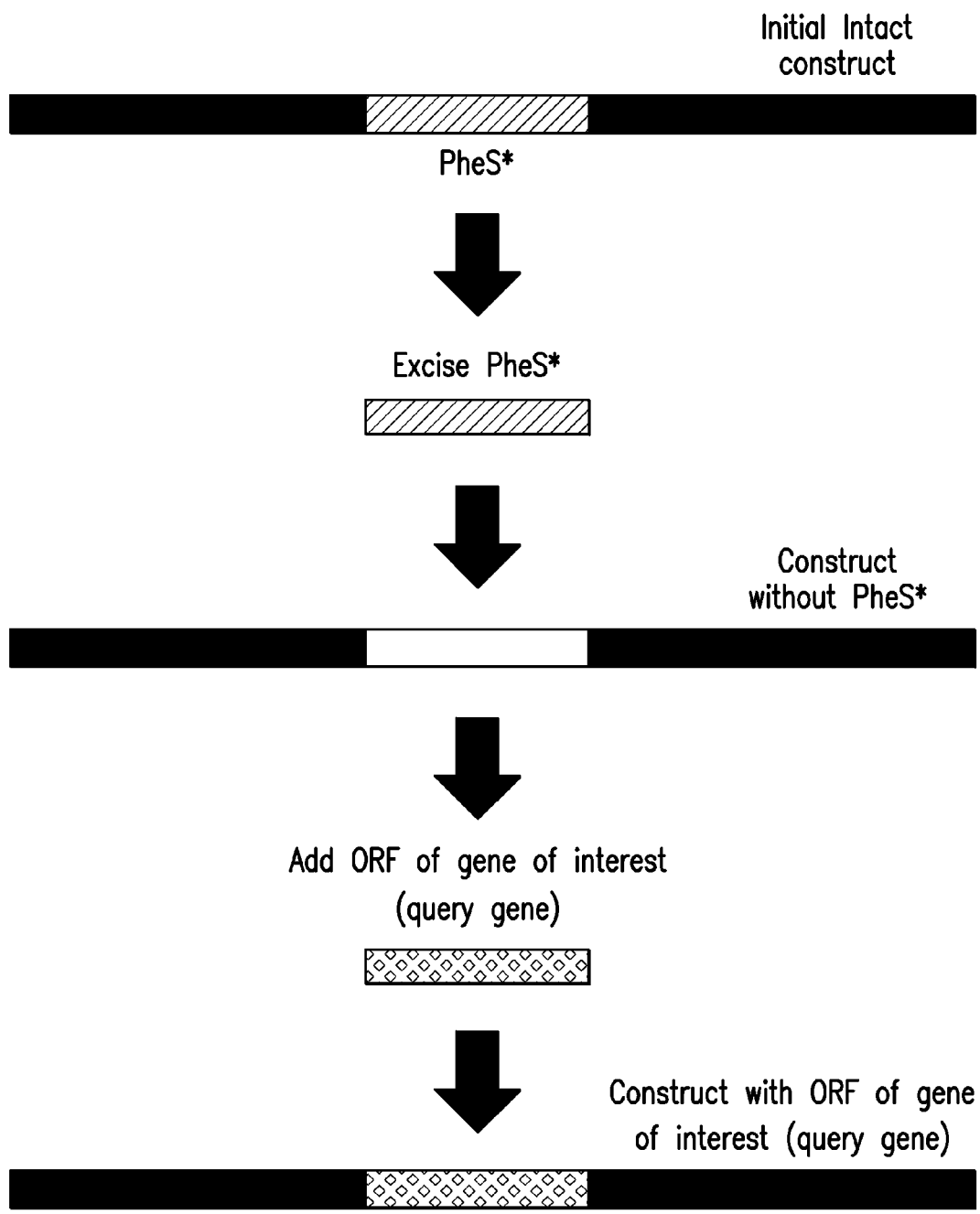
FIG. 3 is a schematic of the swap in which a query gene's open reading frame (ORF) is substituted in place of the PheS* of a disclosed construct.

Disclosed herein are DNA constructs. In an aspect, a disclosed DNA construct can be non-naturally occurring. In an aspect, a disclosed DNA construct can comprise exogenous nucleic acids. In an aspect, a disclosed DNA construct can comprise SEQ ID NO:1. In an aspect, a disclosed DNA construct can comprise SEQ ID NO:2. In an aspect, a disclosed DNA construct can comprise a modified version of SEQ ID NO:2 in that certain nucleotides can be removed and/or other nucleotides can be added. For example, in an aspect, SEQ ID NO:2 can be modified such that the PheS open reading frame is replaced with the open reading frame of a query gene. In an aspect, the nucleotides at positions 4369-5352 can be removed from SEQ ID NO:2 and can be replaced the nucleotides of a query gene. (See FIG. 3).

In an aspect, a DNA construct can comprise a reporter gene under the control of a first sequence of a pair of promoter sequences, a reporter gene for determining incorporation of the DNA construct in the genome, and a copy of a query gene under the control of the second sequence of the pair of promoter sequences, wherein the pair of promoter sequences is under the control of a repressor protein. In an aspect, the pair of promoter sequences can comprise Lambda pR promoter and Lambda pL promoter. In an aspect, the repressor protein can be Lambda repressor (cI).

Disclosed herein are plasmids. In an aspect, a plasmid can be a par⁻ plasmid. In an aspect, a plasmid can comprise a genetic sequence encoding the repressor protein, a reporter gene for determining the presence of the plasmid in the cell, and a selectable marker for plasmid selection. In an aspect, a plasmid can comprise SEQ ID NO:1. In an aspect, a plasmid can comprise SEQ ID NO:2. In an aspect, a plasmid can comprise a modified version of SEQ ID NO:1. In an aspect, a plasmid can comprise a modified version of SEQ ID NO:2. In an aspect, the repressor protein can be Lambda repressor (cI). In an aspect, the Lambda repressor (cI) can repress Lambda pR promoter and Lambda pL promoter.

In an aspect, the disclosed constructs and disclosed plasmids can be used to perform the disclosed methods, such as, for examples, methods for identifying a dominant lethal gene, methods for identifying a second site of suppression, methods for screening for compounds that inhibit distinct gene variants, and methods for identifying cells that cannot tolerate a gene variant.

2. Cells

Disclosed herein are cells. In an aspect, the cells can be *E. coli* cells. In an aspect, a cell can comprise one or more of the constructs, plasmids, and/or nucleic acid molecules disclosed herein. For example, in an aspect, a cell can comprise a DNA construct comprising SEQ ID NO:1. In an aspect, a cell can comprise a DNA construct comprising SEQ ID NO:2. In an aspect, a cell can comprise a DNA construct comprising a modified version of SEQ ID NO:1. In an aspect, a cell can comprise a DNA construct comprising a modified version of SEQ ID NO:2. In an aspect, a cell can comprise an integrated DNA construct, an unstable plasmid, and/or both. In an aspect, the DNA construct can comprise a modified version of SEQ ID NO:2, which modifications include removing certain nucleotides and/or adding other nucleotides. For example, in an aspect, a cell can comprise a DNA construct comprising SEQ ID NO:2 that is modified such that the PheS open reading frame is replaced with the open reading frame of a query gene. In a further aspect, the nucleotides at positions 4369-5352 can be removed from SEQ ID NO:2 and can be replaced the nucleotides of the open reading frame ORF of a query gene (i.e., gene of interest).

Cells disclosed herein are used to perform the disclosed methods, such as, for examples, methods for identifying a dominant lethal gene, methods for identifying a second site of suppression, methods for screening for compounds that inhibit distinct gene variants, and methods for identifying cells that cannot tolerate a gene variant.

3. Nucleic Acid Molecules

Disclosed herein are nucleic acid molecules. In an aspect, the nucleic acid molecules can be isolated. In an aspect, the nucleic acid molecules can be non-naturally occurring. In an aspect, a nucleic acid molecule can comprise SEQ ID NO:1. In an aspect, a nucleic acid molecule can comprise SEQ ID NO:2. In an aspect, a nucleic acid molecule can comprise a modified version of SEQ ID NO:1. In an aspect, a nucleic acid molecule can comprise a modified version of SEQ ID NO:2. For example, a modified version of SEQ ID NO:2 can comprise a modification or modifications that remove certain nucleotides and/or adds other nucleotides. For example, in an aspect, a modified SEQ ID NO:2 can comprise replacing a PheS open reading frame with the open reading frame of a query gene. In an aspect, a modified SEQ ID NO:2 can comprise replacing the nucleotides at positions 4369-5352 with the nucleotides of query gene.

Nucleic acids disclosed herein are used to perform the disclosed methods, such as, for examples, methods for identifying a dominant lethal gene, methods for identifying a second site of suppression, methods for screening for compounds that inhibit distinct gene variants, and methods for identifying cells that cannot tolerate a gene variant.

4. Kits

Disclosed herein are kits. Disclosed herein is a kit comprising cells and a DNA construct comprising SEQ ID NO:1. Disclosed herein is a kit comprising cells and a DNA construct comprising SEQ ID NO:2. Disclosed herein is a kit comprising cells and a DNA construct comprising a modified version of SEQ ID NO:1. Disclosed herein is a kit comprising cells and a DNA construct comprising a modified version of SEQ ID NO:2. In an aspect, the DNA construct can comprise a modified version of SEQ ID NO:2 in that certain nucleotides can be removed and/or other nucleotides can be added. For example, in a further aspect, SEQ ID NO:2 can be modified such that the PheS open reading frame can be replaced with the open reading frame of a query gene. In a further aspect, the nucleotides at positions 4369-5352 can be removed from SEQ ID NO:2 and can be replaced the nucleotides of a query gene. In an aspect, the cells of the disclosed kit can be *E. coli* cells.

Disclosed herein is a kit comprising cells, a DNA construct comprising SEQ ID NO:2, and instructions for replacing PheS in the DNA construct with a query gene. In an aspect, the instructions can teach a DNA construct comprising a modified version of SEQ ID NO:2 in that certain nucleotides can be removed and/or other nucleotides can be added. For example, in a further aspect, the instructions can teach that SEQ ID NO:2 is modified such that the PheS open reading frame can be replaced with the open reading frame of a query gene. In a further aspect, the instructions can teach that the nucleotides at positions 4369-5352 can be removed from SEQ ID NO:2 and can be replaced the nucleotides of a query gene. In an aspect, the cells of the disclosed kit can be *E. coli* cells.

Disclosed herein is a kit comprising cells comprising a stably integrated DNA construct and a par⁻ plasmid, wherein the DNA construct comprises a reporter gene under the control of a first sequence of a pair of promoter sequences, a reporter gene for detecting incorporation of the DNA construct in the genome, and a copy of a query gene under the control of the second sequence of the pair of promoter sequences, and wherein the par⁻ plasmid comprises a genetic sequence encoding a repressor protein, a reporter gene for determining the presence of the plasmid in the cell, and a selectable marker for plasmid selection. In an aspect, the cells of the disclosed kit can be *E. coli* cells. In an aspect, a plasmid comprises SEQ ID NO:1. In an aspect, the repressor protein can be Lambda repressor (cI). In an aspect, the Lambda repressor (cI) can repress Lambda pR promoter and Lambda pL promoter.

In an aspect, the disclosed kits can be used to perform the disclosed methods, such as, for examples, methods for identifying a dominant lethal gene, methods for identifying a second site of suppression, methods for screening for compounds that inhibit distinct gene variants, and methods for identifying cells that cannot tolerate a gene variant.

C. DEFINITIONS

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the amino acid abbreviations are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

As described herein, a query gene is a gene of interest and can be referred to as an interrogated gene. A query gene can be a dominant lethal gene.

Dominant lethal genes are expressed in both homozygotes and heterozygotes and are rarely detected due to their rapid elimination from populations. One example of a disease caused by a dominant lethal allele is Huntington's disease, a neurological disorder in humans, which reduces life expectancy. Because the onset of Huntington's disease is slow, individuals carrying the allele can pass it on to their offspring. This allows the allele to be maintained in the population. Dominant traits can also be maintained in the population through recurrent mutations or if the penetrance of the gene is less than 100%.

Intragenic suppression, as used herein, results from suppressor mutations that occur in the same gene as the original mutation. Intergenic suppression is useful for identifying and studying interactions between molecules, such as proteins. For example, a mutation in a gene that renders it defective in some functional aspect can sometimes be compensated by an additional mutation in the same gene. One example being a change in an enzyme that weakens an interaction with a substrate that is compensated for by a concomitant mutation that strengthens the interaction. Another example being allosteric control in protein dynamics wherein a hindering mutation becomes compensated by a second mutation that restores the functional dynamics.

Intergenic suppression (also referred to as extragenic suppression), as used herein, relieves the effects of a mutation in one gene by a mutation in a different gene. Intergenic suppression is useful for identifying and studying interactions between molecules, such as proteins. For example, a mutation which disrupts the complementary interaction between protein molecules may be compensated for by a second mutation elsewhere in the genome that restores or provides a suitable alternative interaction between those molecules.

As used herein, temperate bacteriophage are characterized by their ability to replicate either by a lytic growth cycle at the expense of a host cell, or by a lysogenic cycle in which the phage genome is incorporated as a prophage into the host cell chromosome.

"Peptide" as used herein refers to any peptide, oligopeptide, polypeptide, gene product, expression product, or protein. For example, a peptide can be an enzyme. A peptide is comprised of consecutive amino acids. Polypeptides encompass naturally occurring or synthetic molecule, and may contain modified amino acids other than the 20 gene-encoded amino acids. Polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide.

In general, the biological activity or biological action of a gene or nucleic acid or peptide refers to any function exhibited or performed by the gene or nucleic acid or peptide that is ascribed to the naturally occurring form of the gene or nucleic acid or peptide as measured or observed in vivo (i.e., in the natural physiological environment of the gene or nucleic acid or peptide) or in vitro (i.e., under laboratory conditions).

The term "enzyme" as used herein refers to any peptide that catalyzes a chemical reaction of other substances without itself being destroyed or altered upon completion of the reaction. Typically, a peptide having enzymatic activity catalyzes the formation of one or more products from one or more substrates. Such peptides can have any type of enzymatic activity including, without limitation, the enzymatic activity or enzymatic activities associated with enzymes such as those disclosed herein.

Mutagenesis as defined herein can be performed by methods commonly known to the art. For example, mutagenesis can be chemical mutagenesis. Examples of known mutagens include nitrosamines, polycyclic hydrocarbons, fungal toxins, aromatic amines, nitrofuran carcinogens, various antineopleastic agents, antibiotic carcinogens such as adriamycin, daunomycin, and mitomycin C, naphthylamine, benzidine, cigarette smoke condensates, bis-choromethyl-eterh, 4-aminobipheny, azoxymethane, aflatoxin Bl, sterigmatocystin, furylfuramide, nitrofuran carcinogens, acetylenic diarylcarbamates, benzo[a]pyrene, 2-acetylaminofluorene, 2-aminofluorene, nitroquinolline-N-oxide, ethylene oxide, hydrazine sulfate, bleomycin, tert-butyhydroperoxide, HC235 extract, methyl methanesulfonic acid, ICRI91, 9-amino acrydine, Danthron, cyclophosphamide, ethyl methanesulfonate, and sodium azide. A list of additional chemicals evaluated as mutagenic is described in Prival et al., 1998 (Mutation Research 412:251-260). In an aspect, the mutagen is N-ethyl-N-nitrosourea. Mutagenesis can occur due to exposure to ultraviolet radiation or other radiant source. Mutagenesis can be accomplished via transposons.

Cells can be obtained from commercial sources such as the American Type Culture Collection (ATCC) and can be prokaryotic or eukaryotic. Cells (e.g., E. coli) can contain the genetic control system disclosed herein. Cells (e.g., E. coli) can contain one or more isolated nucleic acids, such as those isolated nucleic acids disclosed herein. Cells can be grown in liquid media culture or on tissue culture plates. The growth conditions will be dependent upon the specific cells used and such conditions would be known to one of skill in the art. Transfection and growth of host cells is described in Maniatis et al.

As used herein, the terms "optional" or "optionally" means that the subsequently described event or circumstance can or cannot occur, and that the description includes instances where said event or circumstance occurs and instances where it does not.

As used herein, the terms "transformation" and "transfection" mean the introduction of a nucleic acid, e.g., an expression vector, into a recipient cell including introduction of a nucleic acid to the chromosomal DNA of said cell. The art is familiar with various compositions, methods, techniques, etc. used to effect the introduction of a nucleic acid into a recipient cell. The art is familiar with such compositions, methods, techniques, etc. for both eukaryotic and prokaryotic cells. The art is familiar with such compositions, methods, techniques, etc. for the optimization of the introduction and expression of a nucleic acid into and within a recipient cell.

The term "contacting" as used herein refers to bringing a disclosed compound and a cell, target receptor, gene, peptide, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the term "determining" can refer to measuring or ascertaining a quantity or an amount or a change in expression and/or activity level, e.g., of a nucleotide or nucleic acid molecule or transcript or polypeptide. For example, determining the amount of a disclosed transcript or polypeptide in a sample as used herein can refer to the steps that the skilled person would take to measure or ascertain some quantifiable value of the transcript or polypeptide in the sample. The art is familiar with the ways to measure an amount of the disclosed nucleotides, transcripts, polypeptides, etc.

The term "exogenous" as used herein with reference to a nucleic acid and a particular organism refers to any nucleic acid that does not originate from that particular organism as found in nature. "Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism.

As used herein, the term "healthy" refers to cells that demonstrate normal or near normal growth kinetics, normal or near normal cellular metabolism, and normal or near normal cellular morphology.

As used herein, the term "toxic" refers to cells that demonstrate abnormal growth kinetics, abnormal cellular metabolism, and abnormal cellular morphology. Toxic cells are not thriving cells. Toxic cells can be cells that are in distress and/or cells that are dying.

In bacteria, selectable markers include, but are not limited to, genes that confer resistance to antibiotics such as ampicillin, tetracycline, chloramphenicol, streptomycin, spectinomycin, and kanamycin. Selectable markers also include genes that permit the growth of auxotrophic bacteria, such as amino acid synthesis genes, or pyrimidine, purine, sugar, and lipid synthesis genes.

Reporter genes are known to the art and can be used to induce visual characteristics allowing for identification (such as, for example, β-galactosidase, chloramphenicol acetyltransferase, neomycin phosphotransferase, and green fluorescent protein).

As used herein, a par$^-$ plasmid is a plasmid that is unstable in that it is not reliably transferred to progeny or daughter cells. Plasmid partition systems are essential for the stability and thus the survival of low-copy-number plasmids in growing bacterial populations. The partition reaction is responsible for proper intracellular distribution of plasmids in the bacterial cell cycle. The structural biology of plasmid partition is reviewed by Schumacher et al., 2008, which is hereby incorporated by reference for its teachings relating to plasmid partition As used herein, the term "level" refers to the amount of a target molecule in a sample, e.g., a sample from a subject. The amount of the molecule can be determined by any method known in the art and will depend in part on the nature of the molecule (i.e., gene, DNA, RNA, mRNA, cDNA, protein, enzyme, etc.). The art is familiar with quantification methods for nucleotides (e.g., genes, DNA, RNA, cDNA, mRNA, etc.) as well as proteins, polypeptides, enzymes, etc. It is understood that the amount or level of a molecule in a sample need not be determined in absolute terms, but can be determined in relative terms (e.g., when compare to a control or a sham or an untreated sample).

By "modulate" is meant to alter, by increase or decrease. As used herein, a "modulator" can mean a composition that can either increase or decrease the expression level or activity level of a gene or gene product such as a peptide. Modulation in expression or activity does not have to be complete. For example, expression or activity can be modulated by about 10%, 20%, 30%, 40%, 50%, 60%, 70%, 80%, 90%, 95%, 99%, 100% or any percentage in between as compared to a control cell wherein the expression or activity of a gene or gene product has not been modulated by a composition.

Disclosed are the components to be used to prepare a composition of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

The present invention can be understood more readily by reference to the following detailed description of the invention and the Examples included therein.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

D. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Experiments
A. Construction of Genetic Control System

A genetic control system comprising elements of the bacteriophage lambda's immunity/lysogeny control region was designed and implemented in E. coli. Bacteriophage λ is a temperate bacteriophage, meaning that it can reproduce and develop either in a lytic or lysogenic state. When λ infects its bacterial host Escherichia coli, the phage may develop lytically, causing cell lysis with the release of hundreds of progeny virus, or it may abort lytic development by switching off most viral expression, integrate its genome into the bacterial chromosome, and exist as a quiescent prophage in the lysogenic state. Although very stable, the lysogenic or prophage state can be reverted by inducing agents that damage the host DNA, returning the virus λ to its lytic state. These systems of lytic growth, lysogenic growth, and lysogenic induction from the prophage state are excellent model systems for understanding developmental pathways and the switches between these pathways. Within these pathways are sets of intertwined positive and negative regulators of gene expression acting at the transcription and post-transcription level.

Here, the left and right promoters of this region drove expression of a reporter gene and a query gene (i.e., gene of interest), respectively. (See FIG. 1). In the genetic control system disclosed herein, the repressor was expressed from an unstable plasmid that did not reliably partition into daughter cells. Accordingly, if a daughter cell maintained a copy of the plasmid, then the daughter cell expressed repressor and the system was turned off. If the daughter cell did not maintain the plasmid, then the Lambda promoters turned on and both the reporter and query gene were expressed. The repressor plasmid also contained a reporter gene (for example, lacZ) that allowed a determination of whether the cells of a colony maintained the plasmid or lost the plasmid. When the lambda repressor was present, the system was tightly off. When the repressor was absent, both promoters fired strongly.

For example, FIG. 1 shows a schematic of a disclosed genetic control screening system. In FIG. 1, a copy of the query gene (geneX) was introduced in the chromosome and was under the control of the phage Lambda pR promoter. A wild-type copy of the query gene exists elsewhere in the genome. An unstable (par⁻) plasmid encoding the Lambda repressor (cI) and a reporter (LacZ) shuts off expression of the geneX. Other components of the genetic control system included: (i) a GFP reporter expressed from pL that is simultaneously repressed; (ii) a tetracycline resistance gene for selection of the integrated construct; and (iii) an ampicillin-resistance gene (bla) used for plasmid selection.

The unstable plasmid was constructed based on a plasmid called "pRC-7" (gift from Thomas Bernhardt at Harvard). The 5' end of lacZ was constructed, the lambda repressor gene was added, and the lac promoter drove the expression of both the repressor (cI) and lacZ. An ampicillin resistance gene was added so that transformed cells could be selected using ampicillin (i.e., selecting for cells that retained a copy of plasmid). During the screen, no ampicillin was used and the plasmid was readily lost, which resulted in the loss of the blue color and the loss of the repressor.

The integrated genetic system was based on the phage lambda immunity control region. In this region, two strong promoters face away from each other. The repressor protein on the plasmid handcuffed the two promoters and kept the promoters very tightly turned off (i.e., occluded access by polymerase). When the Lambda cI repressor was lost, both promoters fired strongly. Potent terminators prevented transcription past the genes of interest. While the expression level of the query gene was dependent on a number of unpredictable factors (e.g., RNA stability, translation initiation strength, etc.), an optimized translation start sequence was used. Furthermore, a query gene's open reading frame (ORF) was substituted in place of the PheS*. This "swap" is represented in Figure XX. In SEQ ID NO:2, PheS* at nucleotides 4369-5352 was excised using common molecular biology techniques. The production of the copy of the query gene (geneX) was sufficient to interfere with the normal pathway by out-competing the wild-type gene.

B. Validation of Genetic Control System

Following the construction of the genetic control system, a culture of those cells harboring the plasmid was subjected to random mutagenesis. Because de-repression of the wild-type copy of the essential query gene is not toxic, plasmid loss does not impede cell growth, and the colonies become sectored as they lose the repressor plasmid. A mutant library was then screened for cells that require the wild-type copy shut off and dominant-lethal variants of the query gene are identified. Colonies identified by this method contained a toxic form of the query gene that must be repressed for colony development (i.e., dominant-lethality).

The genetic control system was validated using a mutant of the *E. coli* aminoacyl tRNAPhe synthetase gene (pheS$^{A294G}$) that is commonly used for counter-selection in bacteriology. PheS$^{A294G}$ is a "fidelity loss" mutant that charges tRNA$^{Phe}$ with phenylalanine analogs (such as chlorophenylalanine, Cl-Phe). In doing so, the cells die because they cannot make functional proteins when Cl-Phe is present. Wild-type and mutant pheS was placed into the disclosed genetic system. When these cells were plated on media lacking Cl-Phe, the repressor plasmid was not necessary because de-repression of the wild-type or pheS$^{A294G}$ gene was harmless. However, when Cl-Phe was present in the medium, lack of a repressor resulted in cell death in the pheS$^{A294G}$ strain because Cl-Phe was incorporated (FIG. 2).

Figure 2:
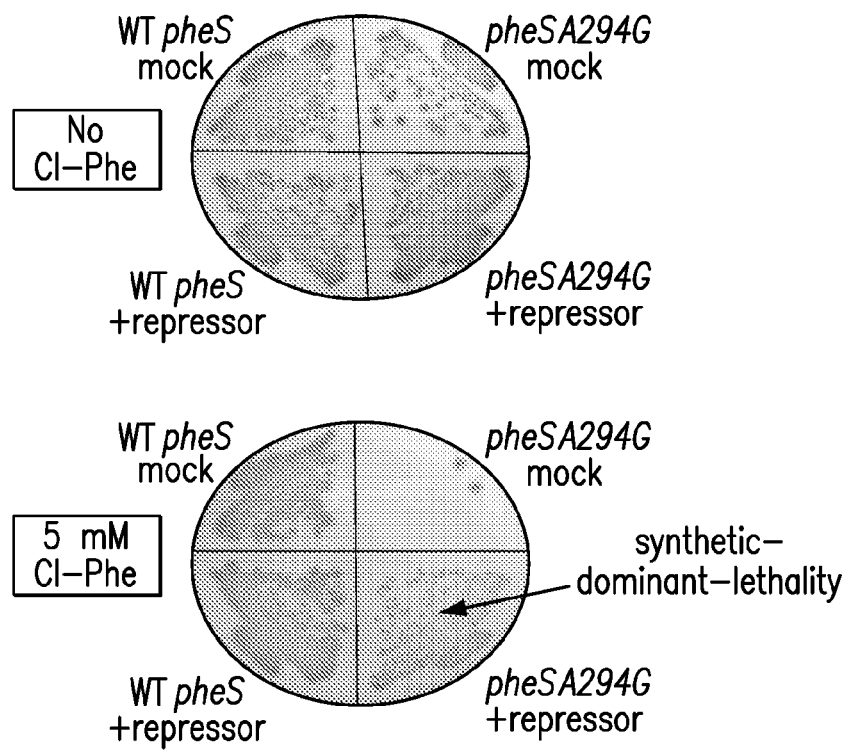
FIG. 2 shows data validating the genetic screening system.

The plate images in FIG. 2 are presented because of the two colonies that arose in the pheS$^{A294G}$ strain containing the mock plasmid. Sequencing of the control locus revealed unprecedented intragenic second-site suppressor mutations in pheS$^{A294G}$. Large libraries of mutated cells containing wild-type pheS on Cl-Phe plates were screened and new dominant-lethal versions for other genetic experiments were recovered. This system is more robust, less costly, and substantially faster than classical replica-plating approaches.

In FIG. 2, *E. coli* strains harboring the screening system were plated with and without Cl-Phe in the medium. On the left of each, wild-type pheS was in the repressible chromosomal construct. The fidelity mutant pheS$^{A294G}$ is on the right. A sectoring phenotype was evident when the cells survive without the unstable plasmid. When the clone of pheS was dominant-lethal, the white cells in the colony did not replicate and the colony was small and dark teal from the LacZ/X-Gal. A mock plasmid lacking Lambda repressor was also tested to confirm that the phenotype was due to repression of the locus.

In an alternative approach, referring to SEQ ID NO:2, a query gene is substituted in the place of the reporter gene such as GFP, thereby leaving PheS* intact. After identifying potential dominant mutants in the screen, the same cells are checked quickly for resistance to Cl-Phe to demonstrate the system is repressed.

C. Identification of Dominant-Lethal Variants and Second-Site Suppressors

Various factors that tightly associate with the targets are likely to regulate, be regulated by, or participate in the biochemical pathway of dominant lethal variants. Because the targets function with the appended tags to support growth, important associations are likely preserved. However, many important biochemical interactions are too weak to allow for co-purification, so genetics is needed to reveal them. By identifying dominant-lethal versions, important functional regions of these proteins are be identified. Recovering second-site suppressor mutants (either intragenic and intergenic) advances the understanding of the targets by revealing functional elements within the protein and networks within the cell.

To identify dominant-lethal genes, each query gene was placed into the genetic control system described herein. Strains were then transformed with the repressor reporter plasmid and chemically mutated with N-ethyl-N-nitrosourea. Mutant libraries with abundant transitions and transversions were generated. The library was then screened for the dark teal colony phenotype associated with repressor-dependence (LacZ). Positive strains were checked by transducing the cells with an antibiotic marker that replaces the query locus. Loss of the dark teal phenotype indicated that the query locus was responsible for repressor dependence. The gene in the mutant was then sequenced.

Because the chromosomes of the mutant stains used to recover the dominant-lethal genes are riddled with unrelated mutations from the chemical mutagenesis, the query locus containing the dominant-lethal genes are phage transduced into a naive host containing the repressor/reporter plasmid. Serial culturing of the resulting strains allows for the accumulation of spontaneous mutants that are no longer dependent on the repressor plasmid. These are recovered by plating on X-gal and identifying healthy white colonies that lost the plasmid. This strategy has successfully recovers second-site suppressors and missense revertants of der and pheS. Extragenic suppressor mutations can be mapped using traditional genetic methods.

E. REFERENCES

The following references, to the extent that they provide exemplary procedural or other details supplementary to those set forth herein, are specifically incorporated herein by reference.

Bernhardt et al. (2004) Screening for synthetic lethal mutants in *Escherichia coli* and identification of EnvC (YibP) as a periplasmic septal ring factor with murein hydrolase activity. Mol. Microbiol. 52(5): 1255-1269.

Schumacher M A. (2008) Structural biology of plasmid partition: uncovering the molecular mechanisms of DNA segregation. Biochem J. 412:1-18.

What is claimed is:

1. An isolated nucleic acid molecule comprising SEQ ID NO:1 or SEQ ID NO:2.

2. A DNA construct comprising the nucleic acid molecule of claim 1.

3. A composition comprising the DNA construct of claim 2.

4. A cell comprising the DNA construct of claim 2.

5. A kit comprising cells and the DNA construct of claim 2.

6. A kit comprising cells, the DNA construct of claim 2, wherein the nucleic acid comprises SEQ ID NO:2, and instructions for replacing PheS in the DNA construct with a query gene.

* * * * *

SEQUENCE LISTING

```
<160> NUMBER OF SEQ ID NOS: 3

<210> SEQ ID NO 1
<211> LENGTH: 13387
<212> TYPE: DNA
<213> ORGANISM: Artificial Sequence
<220> FEATURE:
<223> OTHER INFORMATION: synthetic construct; unstable repressor

<400> SEQUENCE: 1
caattcggga caccatcgaa tggtgcaaaa cctttcgcgg tatggcatga tagcgcccgg      60
aagagagtca attcagggtg gtgaatgtga aaccagtaac gttatacgat gtcgcagagt     120
atgccggtgt ctcttatcag accgtttccc gcgtggtgaa ccaggccagc cacgtttctg     180
cgaaaacgcg ggaaaaagtg gaagcggcga tggcggagct gaattacatt cccaaccgcg     240
tggcacaaca actggcgggc aaacagtcgt tgctgattgg cgttgccacc tccagtctgg     300
ccctgcacgc gccgtcgcaa attgtcgcgg cgattaaatc tcgcgccgat caactgggtg     360
ccagcgtggt ggtgtcgatg gtagaacgaa gcggcgtcga agcctgtaaa gcggcggtgc     420
acaatcttct cgcgcaacgc gtcagtgggc tgatcattaa ctatccgctg gatgaccagg     480
atgccattgc tgtggaagct gcctgcacta atgttccggc gttatttctt gatgtctctg     540
accagacacc catcaacagt attattttct cccatgaaga cggtacgcga ctgggcgtgg     600
agcatctggt cgcattgggt caccagcaaa tcgcgctgtt agcgggccca ttaagttctg     660
tctcggcgcg tctgcgtctg gctggctggc ataaatatct cactcgcaat caaattcagc     720
cgatagcgga acgggaaggc gactggagtg ccatgtccgg ttttcaacaa accatgcaaa     780
tgctgaatga gggcatcgtt cccactgcga tgctggttgc caacgatcag atggcgctgg     840
gcgcaatgcg cgccattacc gagtccgggc tgcgcgttgg tgcggatatc tcggtagtgg     900
gatacgacga taccgaagac agctcatgtt atatcccgcc gtcaaccacc atcaaacagg     960
attttcgcct gctgggccaa accagcgtgg accgcttgct gcaactctct cagggccagg    1020
cggtgaaggg caatcagctg ttgcccgtct cactggtgaa aagaaaaacc accctggcgc    1080
ccaatacgca aaccgcctct ccccgcgcgt tggccgattc attaatgcag ctggcacgac    1140
aggtttcccg actggaaagc gggcagtgag cgcaacgcaa ttaatgtgag ttagctcact    1200
cattaggcac cccaggcttt acactttatg cttccggctc gtatgttgtg tggaattgtg    1260
```

```
agcggataac aatttcacac aggaggtacc ttatgagcac aaaaaagaaa ccattaacac   1320
aagagcagct tgaggacgca cgtcgcctta aagcaattta tgaaaaaaag aaaaatgaac   1380
ttggcttatc ccaggaatct gtcgcagaca agatggggat ggggcagtca ggcgttggtg   1440
ctttatttaa tggcatcaat gcattaaatg cttataacgc cgcattgctt gcaaaaattc   1500
tcaaagttag cgttgaagaa tttagccctt caatcgccag agaaatctac gagatgtatg   1560
aagcggttag tatgcagccg tcacttagaa gtgagtatga gtaccctgtt ttttctcatg   1620
ttcaggcagg gatgttctca cctgagctta gaacctttac caaaggtgat gcggagagat   1680
gggtaagcac aaccaaaaaa gccagtgatt ctgcattctg gcttgaggtt gaaggtaatt   1740
ccatgaccgc accaacaggc tccaagccaa gctttcctga cggaatgtta attctcgttg   1800
accctgagca ggctgttgag ccaggtgatt tctgcatagc cagacttggg ggtgatgagt   1860
ttaccttcaa gaaactgatc agggatagcg gtcaggtgtt tttacaacca ctaaacccac   1920
agtacccaat gatcccatgc aatgagagtt gttccgttgt ggggaaagtt atcgctagtc   1980
agtggcctga agagacgttt ggctaacggc cgaggagata gcttatggat tcactggccg   2040
tcgttttaca acgtcgtgac tgggaaaacc ctggcgttac ccaacttaat cgccttgcag   2100
cacatccccc tttcgccagc tggcgtaata gcgaagaggc ccgcaccgat cgcccttccc   2160
aacagttgcg cagcctgaat ggcgaatggc gctttgcctg gtttccggca ccagaagcgg   2220
tgccggaaag ctggctggag tgcgatcttc ctgaggccga tactgtcgtc gtcccctcaa   2280
actggcagat gcacggttac gatgcgccca tctacaccaa cgtaacctat cccattacgg   2340
tcaatccgcc gtttgttccc acggagaatc cgacgggttg ttactcgctc acatttaatg   2400
ttgatgaaag ctggctacag gaaggccaga cgcgaattat ttttgatggc gttaactcgg   2460
cgtttcatct gtggtgcaac gggcgctggg tcggttacgg ccaggacagt cgtttgccgt   2520
ctgaatttga cctgagcgca tttttacgcg ccggagaaaa ccgcctcgcg gtgatggtgc   2580
tgcgttggag tgacggcagt tatctggaag atcaggatat gtggcggatg agcggcattt   2640
tccgtgacgt ctcgttgctg cataaaccga ctacacaaat cagcgatttc catgttgcca   2700
ctcgctttaa tgatgatttc agccgcgctg tactggaggc tgaagttcag atgtgcggcg   2760
agttgcgtga ctacctacgg gtaacagttt ctttatggca gggtgaaacg caggtcgcca   2820
gcggcaccgc gcctttcggc ggtgaaatta tcgatgagcg tggtggttat gccgatcgcg   2880
tcacactacg tctcaacgtc gaaacccga aactgtggag cgccgaaatc ccgaatctct   2940
atcgtgcggt ggttgaactg cacaccggcg acggcacgct gattgaagca gaagcctgcg   3000
atgtcggttt ccgcgaggtg cggattgaaa atggtctgct gctgctgaac ggcaagccgt   3060
tgctgattcg aggcgttaac cgtcacgagc atcatcctct gcatggtcag gtcatggatg   3120
agcagacgat ggtgcaggat atcctgctga tgaagcagaa caactttaac gccgtgcgct   3180
gttcgcatta tccgaaccat ccgctgtggt acacgctgtg cgaccgctac ggcctgtatg   3240
tggtggatga agccaatatt gaaacccacg gcatggtgcc aatgaatcgt ctgaccgatg   3300
atccgcgctg gctaccggcg atgagcgaac gcgtaacgcg aatggtgcag cgcgatcgta   3360
atcacccgag tgtgatcatc tggtcgctgg ggaatgaatc aggccacggc gctaatcacg   3420
acgcgctgta tcgctggatc aaatctgtcg atccttcccg cccggtgcag tatgaaggcg   3480
gcggagccga caccacggcc accgatatta tttgcccgat gtacgcgcgc gtggatgaag   3540
accagcccct tcccggctgt gccgaaatgg tccatcaaaaa atggctttcg ctacctggag   3600
```

```
agacgcgccc gctgatcctt tgcgaatacg cccacgcgat gggtaacagt cttggcggtt    3660
tcgctaaata ctggcaggcg tttcgtcagt atccccgttt acagggcggc ttcgtctggg    3720
actgggtgga tcagtcgctg attaaatatg atgaaaacgg caacccgtgg tcggcttacg    3780
gcggtgattt tggcgatacg ccgaacgatc gccagttctg tatgaacggt ctggtctttg    3840
ccgaccgcac gccgcatcca gcgctgacgg aagcaaaaca ccagcagcag ttttccagt     3900 tccgttatc cgggcaaacc atcgaagtga ccagcgaata cctgttccgt catagcgata    3960
acgagctcct gcactggatg gtggcgctgg atggtaagcc gctggcaagc ggtgaagtgc    4020
ctctggatgt cgctccacaa ggtaaacagt tgattgaact gcctgaacta ccgcagccgg    4080
agagcgccgg gcaactctgg ctcacagtac gcgtagtgca accgaacgcg accgcatggt    4140
cagaagccgg gcacatcagc gcctggcagc agtggcgtct ggcggaaaac ctcagtgtga    4200
cgctccccgc cgcgtcccac gccatcccgc atctgaccac cagcgaaatg gattttttgca   4260 tcgagctggg taataagcgt tggcaattta accgccagtc aggctttctt tcacagatgt    4320
ggattggcga taaaaaacaa ctgctgacgc cgctgcgcga tcagttcacc cgtgcaccgc    4380
tggataacga cattggcgta agtgaagcga cccgcattga ccctaacgcc tgggtcgaac    4440
gctggaaggc ggcgggccat taccaggccg aagcagcgtt gttgcagtgc acggcagata    4500
cacttgctga tgcggtgctg attacgaccg ctcacgcgtg gcagcatcag gggaaaacct    4560
tatttatcag ccggaaaacc taccggattg atggtagtgg tcaaatggcg attaccgttg    4620
atgttgaagt ggcgagcgat acaccgcatc cggcgcggat tggcctgaac tgccagctgg    4680
cgcaggtagc agagcgggta aactggctcg gattagggcc gcaagaaaac tatcccgacc    4740
gccttactgc cgcctgtttt gaccgctggg atctgccatt gtcagacatg tatacccgt    4800 acgtcttccc gagcgaaaac ggtctgcgct gcgggacgcg cgaattgaat tatggccac    4860 accagtggcg cggcgacttc cagttcaaca tcagccgcta cagtcaacag caactgatgg    4920
aaaccagcca tcgccatctg ctgcacgcgg aagaaggcac atggctgaat atcgacggtt    4980
tccatatggg gattggtggc gacgactcct ggagcccgtc agtatcggcg aattacagc    5040 tgagcgccgt tcgctaccat taccagttgg tctggtgtca aaataataa taaccgggca    5100 ggccatgtct gcccgtattt cgcgtaagga atccattat gtactattta aaaaacacaa    5160
acttttggat gttcggttta ttcttttttct tttactttttt tatcatggga gcctacttcc    5220 cgttttttccc gatttggcta catgacatca accatatcag caaaagtgat acgggtatta    5280 ttttttgccgc tatttctctg ttctcgctat tattccaacc gctgtttggt ctgctttctg    5340
acaaactcgg gctgcgcaaa tacctgctgt ggattattac cggcatgtta gtgatgtttg    5400
cgccgttctt tattttttatc ttcgggccac tgttacaata caacatttta gtaggatcga    5460
ttgttggtgg tatttatcta ggcttttgtt ttaacgccgg tgcgccagca gtagaggcat    5520
ttattgagaa agtcagccgt cgcagtaatt tcgaatttgg tcgcgcgcgg atgtttggct    5580
gtgttggctg ggcgctgtgt gcctcgattg tcggcatcat gttcaccatc aataatcagt    5640
ttgttttctg gctgggctct ggctgtgcac tcatcctcgc cgttttactc ttttttcgcca    5700 aaacggatgc gccctcttct gccacggttg ccaatgcgt aggtgccaac cattcggcat    5760
ttagccttaa gctggcactg aactgttca gacagccaaa actgtggttt ttgtcactgt    5820
atgttattgg cgtttcctgc acctacgatg ttttttgacca acagtttgct aatttcttta    5880
cttcgttctt tgctaccggt gaacagggta cgcgggtatt tggctacgta acgacaatgg    5940
gcgaattact taacgcctcg attatgttct ttgcgccact gatcattaat cgcatcggtg    6000
```

```
ggaaaaacgc cctgctgctg gctggcacta ttatgtctgt acgtattatt ggctcatcgt    6060
tcgccacctc agcgctggaa gtggttattc tgaaaacgct gcatatgttt gaagtaccgt    6120
tcctgctggt gggctgcttt aaatatatta ccagccagtt tgaagtgcgt ttttcagcga    6180
cgatttatct ggtctgtttc tgcttcttta agcaactggc gatgattttt atgtctgtac    6240
tggcgggcaa tatgtatgaa agcatcggtt tccagggcgc ttatctggtg ctgggtctgg    6300
tggcgctggg cttcaccttn atttccgtgt tcacgcttag cggccccggc ccgctttccc    6360
tgctgcgtcg tcaggtgaat gaagtcgctt aagcaatcaa tgtcggatgc ggcgcgacgc    6420
ttatccgacc aacatatcat aacggagtga tcgcattgaa catgccaatg accgaaagaa    6480
taagagcagg caagctattt accgatatgt gcgaaggctt accggaaaaa agacttcgtg    6540
ggaaaacgtt aatgtatgag tttaatcact cgcatccatc agaagttgaa aaaagagaaa    6600
gcctgattaa agaaatgttt gccacggtag gggaaaacgc ctgggtagaa ccgcctgtct    6660
atttctctta cggttccaac atccatatag gccgcaattt ttatgcaaat ttcaatttaa    6720
ccattgtcga tgactacacg gtaacaatcg gtgataacgt actgattgca cccaacgtta    6780
ctctttccgt tacgggacac cctgtacacc atgaattgag aaaaaacggc gagatgtact    6840
cttttccgat aacgattggc aataacgtct ggatcggaag tcatgtggtt attaatccag    6900
gcgtcaccat cggggataat tctgttattg gcgcgggtag tatcgtcaca aaagacattc    6960
caccaaacgt cgtggcggct ggcgttcctt gtcgggttat tcgcgaaata aacgaccggg    7020
ataagcacta ttatttcaaa gattataaag ttgaatcgtc agtttaaatt ataaaaattg    7080
cctgatacgc tgcgcttatc aggcctacaa gttcagcgat ctacattagc cgcatccggc    7140
atgaacaaag cgcaggaaca agcgtcgcat catgcctctt tgacccacag ctgcggaaaa    7200
cgtactggtg caaaacgcag ggttatgatc atcagcccaa cgacgcacag cgcatgaaat    7260
gcccagtcca tcaggtaatt gccgctgata ctacgcagca cgccagaaaa ccacggggca    7320
agcccggcga tgataaaacc gattccctgc ataaacgcca ccagcttgcc agcaatagcc    7380
ggttgcacag agtgatcgag cgccagcagc aaacagagcg gaaacgcgcc gcccagacct    7440
aacccacaca ccatcgccca aataccggc aattgcatcg gcagccagat aaagccgcag    7500
aaccccacca gttgtaacac cagcgccagc attaacagtt gcgccgatc ctgatggcga    7560 gccatagcag gcatcagcaa agctcctgcg gcttgcccaa gcgtcatcaa tgccagtaag    7620
gaaccgctgt actgcgcgct ggcaccaatc tcaatataga agcgggtaa ccaggcaatc    7680 aggctggcgt aaccgccgtt aatcagaccg aagtaaacac ccagcgtcca cgcgcgggga    7740
gtgaatacca cgcgaaccgg agtggttgtt gtcttgtggg aagaggcgac ctcgcgggcg    7800
ctttgccacc accaggcaaa gagcgcaaca acggcaggca gcgccaccag gcgagtgttt    7860
gataccaggt ttcgctatgt tgaactaacc agggcgttat ggcggcacca gcccaccgc    7920 cgcccatcag agccgcggac cacagcccca tcaccagtgg cgtgcgctgc tgaaaccgcc    7980
gtttaatcac cgaagcatca ccgcctgaat gatgccgatc cccaccccac caagcagtgc    8040
gctgctaagc agcagcgcac tttgcgggta aagctcacgc atcaatgcac cgacggcaat    8100
cagcaacaga ctgatggcga cactgcgacg ttcgctgaca tgctgatgaa gccagcttcc    8160
ggccagcgcc agcccgccca tggtaaccac cggcagagcg gcccactgcc acggctccta    8220
ctgctactcg cgtaacaatc taagtatgt gccacggact gacgcaatcg ttaaattgac    8280
actatttgat ggcgtaattt cgaccatccg tgatacattg aggctgttcc ctgggggtcg    8340
```

```
ttaccttcca cgagcaaaac acgtagcccc ttcagagcca gatcctgagc aagatgaaca    8400
gaaactgagg ttttgtaaac gccacctttta tgggcagcaa ccccgatcac cggtggaaat    8460
acgtcttcag cacgtcgcaa tcgcgtacca aacacatcac gcatatgatt aatttgttca    8520
attgtataac caacacgttg ctcaacccgt cctcgaattt ccatatccgg gtgcggtagt    8580
cgccctgctt tctcggcatc tctgatagcc tgagaagaaa ccccaactaa atccgctgct    8640
tcacctattc tccagcgccg ggttattttc ctcgcttccg ggctgtcatc attaaactgt    8700
gcaatggcga tagccttcgt catttcatga ccagcgttta tgcactggtt aagtgtttcc    8760
atgagtttca ttctgaacat cctttaatca ttgctttgcg ttttttttatt aaatcttgca    8820
atttactgca aagcaacaac aaaatcgcaa agtcatcaaa aaaccgcaaa gttgtttaaa    8880
ataagagcaa cactacaaaa ggagataaga agagcacata cctcagtcac ttattatcac    8940
tagcgctcgc cgcagccgtg taaccgagca tagcgagcga actggcgagg aagcaaagaa    9000
gaactgttct gtcagatagc tcttacgctc agcgcaagaa gaaatatcca ccgtgggaaa    9060
aactccaggt agaggtacac acgcggatag ccaattcaga gtaataaact gtgataatca    9120
accctcatca atgatgacga actaaccccc gatatcaggt cacatgacga agggaaagag    9180
aaggaaatca actgtgacaa actgccctca aatttggctt ccttaaaaat tacagttcaa    9240
aaagtatgag aaaatccatg caggctgaag gaaacagcaa aactgtgaca aattaccctc    9300
agtaggtcag aacaaatgtg acgaaccacc ctcaaatctg tgacagataa ccctcagact    9360
atcctgtcgt catggaagtg atatcgcgga aggaaaatac gatatgagtc gtctggcggc    9420
ctttcttttt ctcaatgtat gagaggcgca ttggagttct gctgttgatc tcattaacac    9480
agacctgcag gaagcggcgg cggaagtcag gcatacgctg gtaactttga ggcagctggt    9540
aacgctctat gatccagtcg attttcagag agacgatgcc tgagccatcc ggcttacgat    9600
actgacacag ggattcgtat aaacgcatgg catacggatt ggtgatttct tttgtttcac    9660
taagccgaaa ctgcgtaaac cggttctgta acccgataaa gaagggaatg agatatgggt    9720
tgatatgtac actgtaaagc cctctggatg gactgtgcgc acgtttgata aaccaaggaa    9780
aagattcata gcctttttca tcgccggcat cctcttcagg gcgataaaaa accacttcct    9840
tccccgcgaa actcttcaat gcctgccgta tatccttact ggcttccgca gaggtcaatc    9900
cgaatatttc agcatattta gcaacatgga tctcgcagat accgtcatgt tcctgtaggg    9960
tgccatcaga ttttctgatc tggtcaacga acagatacag catacgtttt tgatcccggg   10020
agagactata tgccgcctca gtgaggtcgt ttgactggac gattcgcggg ctatttttac   10080
gtttcttgtg attgataacc gctgtttccg ccatgacaga tccatgtgaa gtgtgacaag   10140
tttttagatt gtcacactaa ataaaaaaga gtcaataagc agggataact tgtgaaaaa   10200
acagcttctt ctgagggcaa tttgtcacag ggttaagggc aatttgtcac agacaggact   10260
gtcatttgag ggtgatttgt cacactgaaa gggcaatttg tcaacacacc ttctctagaa   10320
ccagcatgga taaaggccta caaggcgctc taaaaaagaa gatctaaaaa ctataaaaaa   10380
aataattata aaaatatccc cgtggataag tggataaccc caagggaagt tttttcaggc   10440
atcgtgtgta agcagaatat ataagtgctg ttccctggtg cttcctcgct cactcgaggg   10500
cttcgccctg tcgctcgact gcggcgagca ctactggctg taaaaggaca gaccacatca   10560
tggttctgtg ttcattaggt tgttctgtcc attgctgaca taatccgctc cacttcaacg   10620
taacaccgca cgaagatttc tattgttcct gaaggcatat tcaaatcgtt ttcgttaccg   10680
cttgcaggca tcatgacaga acactacttc ctataaacgc tacacaggct cctgagatta   10740
```

```
ataatgcgga tctctacgat aatgggagat tttcccgact gtttcgttcg cttctcagtg   10800
gataacagcc agcttctctg tttaacagac aaaaacagca tatccactca gttccacatt   10860
tccatataaa ggccaaggca tttattctca ggataattgt ttcagcatcg caaccgcatc   10920
agactccggc atcgcaaact gcaccggtg ccgggcagcc acatccagcg caaaaaccttt   10980
cgtgtagact tccgttgaac tgatggactt atgtcccatc aggctttgca gaactttcag   11040
cggtataccg gcatacagca tgtgcatcgc ataggaatgg cggaacgtat gtggtgtgac   11100
cggaacagag aacgtcacac cgtcagcagc agcggcggca accgcctccc caatccaggt   11160
cctgaccgtt ctgtccgtca cttcccagat ccgcgctttc tctgtccttc ctgtgcgacg   11220
gttacgccgc tccatgggta ttttcagtgt tgccaccatc gtctgcagct ggctgacgta   11280
ccaggagtca gagagcggaa ccagccggtg agtctgctga ccggcgggca ttctccccgc   11340
cgtcctggca gcttttttcgg tccgttgttt cagggtcgca agctgcacaa acggatacgg   11400
aggcgcaagc gaaaaatccc cccgcgtcag cgccagtgct tcattaatgc gtgctccggt   11460
gttccacagt gtggccagca gcatcttgcg gtgcagatcc gggacgtaat ggagcagggc   11520
actcacttcc ggagccagca gatattttgg cagttcatca tggaccatcg acatctggcg   11580
aagtgccaga gctgccggat aatcaatggc aacaggcagc gatgcaggct gcccggcaga   11640
atacactgcc gaggcgtttc cccctggaag ctccctcgtg cgctctcctg ttccgaccct   11700
gccgcttacc ggatacctgt ccgcctttct cccttcggga agcgtggcgc tttctcatag   11760
ctcacgctgt aggtatctca gttcggtgta ggtcgttcgc tccaagctgg gctgtgtgca   11820
cgaaccccc gttcagcccg accgctgcgc cttatccggt aactatcgtc ttgagtccaa   11880
cccggtaaga cacgacttat cgccactggc agcagccact ggtaacagga ttagcagagc   11940
gaggtatgta ggcggtgcta cagagttctt gaagtggtgg cctaactacg gctacactag   12000
aaggacagta tttggtatct gcgctctgct gaagccagtt accttcggaa aaagagttgg   12060
tagctcttga tccggcaaac aaaccaccgc tggtagcggt ggttttttg tttgcaagca   12120
gcagattacg cgcagaaaaa aaggatctca agaagatcct ttgatctttt ctacggggtc   12180
tgacgctcag tggaacgaaa actcacgtta agggattttg gtcatgagat tatcaaaaag   12240
gatcttcacc tagatccttt taaattaaaa atgaagtttt aaatcaatct aaagtatata   12300
tgagtaaact tggtctgaca gttaccaatg cttaatcagt gaggcaccta tctcagcgat   12360
ctgtctattt cgttcatcca tagttgcctg actccccgtc gtgtagataa ctacgatacg   12420
ggagggctta ccatctggcc ccagtgctgc aatgataccg cgagacccac gctcaccggc   12480
tccagattta tcagcaataa accagccagc cggaagggcc gagcgcagaa gtggtcctgc   12540
aactttatcc gcctccatcc agtctattaa ttgttgccgg gaagctagag taagtagttc   12600
gccagttaat agtttgcgca acgttgttgc cattgctgca ggcatcgtgg tgtcacgctc   12660
gtcgtttggt atggcttcat tcagctccgg ttcccaacga tcaaggcgag ttacatgatc   12720
ccccatgttg tgcaaaaaag cggttagctc cttcggtcct ccgatcgttg tcagaagtaa   12780
gttggccgca gtgttatcac tcatggttat ggcagcactg cataattctc ttactgtcat   12840
gccatccgta agatgctttt ctgtgactgg tgagtactca accaagtcat tctgagaata   12900
gtgtatgcgg cgaccgagtt gctcttgccc ggcgtcaaca cgggataata ccgcgccaca   12960
tagcagaact ttaaaagtgc tcatcattgg aaaacgttct cggggcgaa aactctcaag   13020
gatcttaccg ctgttgagat ccagttcgat gtaacccact cgtgcaccca actgatcttc   13080
```

| | |
|---|---|
| agcatctttt actttcacca gcgtttctgg gtgagcaaaa acaggaaggc aaaatgccgc | 13140 |
| aaaaaaggga ataagggcga cacggaaatg ttgaatactc atactcttcc tttttcaata | 13200 |
| ttattgaagc atttatcagg gttattgtct catgagcgga tacatatttg aatgtattta | 13260 |
| gaaaaataaa caatagggg ttccgcgcac atttccccga aaagtgccac ctgacgtcta | 13320 |
| agaaaccatt atsatcatga cattaaccta taaaaatagg cgtatcacga ggccctttcg | 13380 |
| тctтcaa | 13387 |

<210> SEQ ID NO 2
<211> LENGTH: 6970
<212> TYPE: DNA
<213> ORGANISM: Artificial Sequence
<220> FEATURE:
<223> OTHER INFORMATION: synthetic construct; repressor reporter

<400> SEQUENCE: 2

| | |
|---|---|
| tcaaacggca cattcagagt gcgacggaca aaacttgctc caccgtcaca ggctaccagc | 60 |
| cactgggctt tgactatttc ccgctgccct tctgccgttt tcaggtgcaa ggtcacttcg | 120 |
| tcatcttgct gactgaaggc ctccagctcg cgggaaaaca agcagcgcac attcggaaaa | 180 |
| cgcgacaccc cttccagcat caccgcatcg acctgcggct gaataaaggc gttacggcgc | 240 |
| ggccagccaa attcatcggt cattggctga atatcagcaa acagcggcc tttcggggtg | 300 |
| agaaaacgca tcgcgtgcca cggcgtagtg tgcggcagaa catcatcgac caggccgacc | 360 |
| gactgcatgg tgcgcagcgc ctcgtcatca ataccaatcg cacgcgggta gtcgatcaac | 420 |
| ttatcgagtt tctccaccac cagcacgtca atgcccatct ggccgagata gttcgccatc | 480 |
| atcagcccaa ccgggccggc accagcgatc gccacctgaa cgctatggtt aacagcaggc | 540 |
| tggatgtcag ggtgttgtat tgccatttca gtacctcacg actcggacaa aatgtcgttg | 600 |
| cgcgcacagt acagcgcaac ttattttgtt aaaaacatgt aaatgatttt ttattgtgcg | 660 |
| ctcagtatag gaagggtgtt tcggctaca atcaaaacat gcccgaatgt gcaccaggtg | 720 |
| caccacgttg ttttaactat agaaatgtca attaatatgc agaacaatga gcagacggaa | 780 |
| tacaaaaccg tgcgcggctt aacccgcggt ctaatgttat taaatatgtt aaataaactt | 840 |
| gatggcggtg ccagcgtcgg gctgctggcg gaactcagcg gcctgcatcg caccactgtg | 900 |
| cggcgactgc tggagacgct gcaggaagag ggatatgtcc gccgtagccc ctccgatgat | 960 |
| agttttcgac tgaccatcaa agtgcggcaa ttaagcgaag gatttcgtga cgaacagtgg | 1020 |
| atttctgcac tggcggcccc actgctgggc gatctgttgc gcgaagtggt atggccgaca | 1080 |
| gatgtgtcca cgctggatgt tgatgcaatg gtggtacgcg aaaccactca ccgtttcagc | 1140 |
| cgcttatcct ttcaccgggc aatggtcggg cgacgtttgc cgcttctgaa accgcctcg | 1200 |
| ggcctgacct ggctggcctt tgcccggaa caagaccgca aggaattaat cgaaatgtta | 1260 |
| gcctcccgcc ccggtgatga ctatcaactg gcacgggaac cgttaaagct ggaagccatt | 1320 |
| ctggcgcgcg cgcgcaaaga gggttacgga cagaactacc gcggctggga tcaggaggag | 1380 |
| aagatcgcct ctatcgccgt accgctgcgc agtgaacaac gggtgattgg ctgtctgaat | 1440 |
| ctggtgtata tggcgagcgc aatgaccatt gaacaggcag cggaaaagca tcttccggcg | 1500 |
| ctacaacggg tagcaaaaca gatcgaagaa ggggttgaat cgcaggctat tctggtggcc | 1560 |
| ggaaggcgaa gcggcatgca tttacgttga caccatcgag cgaactccgg gacgctcagt | 1620 |
| aatgtgacga tagctgaaaa ctgtacgata aaccaaaaaa tcgtcgggga cattgtaaag | 1680 |
| gcggcgagcg cggcttttcc gcgccagcgt gaaagcagtg tggactggcc gtcaggtacc | 1740 |

```
cgtactgtca ccgtgaccga tgaccatcct tttgatcgcc agatagtggt gcttccgctg   1800
acgtttcgcg gaagtaagcg tactgtcagc ggcaggacaa cgtattcgat gtgttatctg   1860
aaagtactga tgaacggtgc ggtgatttat gatggcgcgg cgttagtctg taatcccagc   1920
agctgttaca aactcaagaa ggaccatgtg gtcacgcttc tcgttgggat ctttcgaaag   1980
ggcagattgt gtggacaggt aatggttgtc tggtaaaagg acagggccat cgccaattgg   2040
agtattttgt tgatgatggt ctgctagttg aacgcttcca tcttcaatgt tgtgtctaat   2100
tttgaagtta actttgattc cattcttttg tttgtctgcc atgatgtata cattgtgtga   2160
gttatagttg tattccaatt tgtgtccaag aatgtttcca tcttctttaa aatcaatacc   2220
ttttaactcg attctattaa caagggtatc accttcaaac ttgacttcag cacgtgtctt   2280
gtagttcccg tcatctttga aaatatagt tctttcctgt ataaccctt cgggcatggc     2340 actcttgaaa aagtcatgct gtttcatatg atctgggtat ctcgcaaagc attgaacacc   2400
ataaccgaaa gtagtgacaa gtgttggcca tggaacaggt agttttccag tagtgcaaat   2460
aaatttaagg gtaagttttc cgtatgttgc atcaccttca ccctctccac tgacagaaaa   2520
tttgtgccca ttaacatcac catctaattc aacaagaatt gggacaactc cagtgaaaag   2580
ttcttctcct ttacgcatgg tctgtttcct gcgtatcaca caccccaaag ccttctgctt   2640
tgaatgctgc ccttcttcag ggcttaattt ttaagagcgt caccttcatg gtggtcagtg   2700
cgtcctgctg atgtgctcag tatcaccgcc agtggtattt atgtcaacac cgccagagat   2760
aatttatcac cgcagatggt tatctgtatg tttttatat gaatttattt tttgcagggg    2820
ggcattgttt ggtaggtgag agatctgaat tgctatgttt agtgagttgt atctatttat   2880
ttttcaataa atacaattgg ttatgtgttt tgggggcgat cgtgaggcaa agaaaacccg   2940
gcgctgaggc cgggttaggt cgaggtggcc cggctccatg caccgcgacg caacgcgggg   3000
aggcagacaa ggtatagggc ggcgcctaca atccatgcca acccgttcca tgtgctcgcc   3060
gaggcggcat aaatcgccgt gacgatcagc ggtccagtga tcgaagttag ctggtaagga   3120
gccgcgagcg atccttgaag ctgtccctga tggtcgtcat ctacctgcct ggacagcatg   3180
gcctgcaacg cgggcatccc gatgccgccg gaagcgagaa gaatcataat ggggaaggcc   3240
atccagcctc gcgtcgcgaa cgccagcaag acgtagccca gcgcgtcggc cgccatgccg   3300
gcgataatgg cctgcttctc gccgaaacgt ttggtggcgg gaccagtgac gaaggcttga   3360
gcgagggcgt gcaagattcc gaataccgca agcgacaggc cgatcatcgt cgcgctccag   3420
cgaaagcggt cctcgccgaa aatgacccag agcgctgccg gcacctgtcc tacgagttgc   3480
atgataaaga agacagtcat aagtgcggcg acgatagtca tgccccgcgc ccaccggaag   3540
gagctgactg ggttgaaggc tctcaagggc atcggtcgac gctctccctt atgcgactcc   3600
tgcattagga agcagcccag tagtaggttg aggccgttga gcaccgccgc cgcaaggaat   3660
ggtgcatgca aggagatggc gcccaacagt cccccggcca cggggcctgc caccataccc   3720
acgccgaaac aagcgctcat gagcccgaag tggcgagccc gatcttcccc atcggtgatg   3780
tcggcgatat aggcgccagc aaccgcacct gtggcgccgg tgatgccggc cacgatgcgt   3840
ccggcgtaga ggatccacag gacgggtgtg gtcgccatga tcgcgtagtc gatagtggct   3900
ccaagtagcg aagcgagcag gactgggcgg cggccaaagc ggtcggacag tgctccgaga   3960
acgggtgcgc atagaaattg catcaacgca tatagcgcta gcagcacgcc atagtgactg   4020
gcgatgctgt cggaatggac gatatcccgc aagaggcccg gcagtaccgg cataaccaag   4080
```

```
cctatgccta cagcatccag ggtgacggtg ccgaggatga cgatgagcgc attgttagat    4140
ttcatacacg gtgcctgact gcgttagcaa tttaactgtg ataaactacc gcattaaagc    4200
ttatcgatga taagctgtca acatgagaa ttacaactta tatcgtatgg ggctgacttc     4260
aggtgcatac gttaaatcta tcaccgcaag ggataaatat ctaacaccgt gcgtgttgac    4320
tattttacct ctggcggtga taatggttgc atgtactaag gaggttgtat gtcacatctc    4380
gcagaactgg ttgccagtgc gaaggcggcc attagccagg cgtcagatgt tgccgcgtta    4440
gataatgtgc gcgtcgaata tttgggtaaa aaagggcact taacccttca gatgacgacc    4500
ctgcgtgagc tgccgccaga agagcgtccg gcagctggtg cggttatcaa cgaagcgaaa    4560
gagcaggttc agcaggcgct gaatgcgcgt aaagcggaac tggaaagcgc tgcactgaat    4620
gcgcgtctgg cggcggaaac gattgatgtc tctctgccag gtcgtcgcat tgaaaacggc    4680
ggtctgcatc cggttacccg taccatcgac cgtatcgaaa gtttcttcgg tgagcttggc    4740
tttaccgtgg caaccgggcc ggaaatcgaa gacgattatc ataacttcga tgctctgaac    4800
attcctggtc accaccggc gcgcgctgac cacgacactt tctggtttga cactacccgc    4860
ctgctgcgta cccagacctc tggcgtacag atccgcacca tgaaagccca gcagccaccg    4920
attcgtatca tcgcgcctgg ccgtgtttat cgtaacgact acgaccagac tcacacgccg    4980
atgttccatc agatggaagg tctgattgtt gataccaaca tcagctttac caacctgaaa    5040
ggcacgctgc acgacttcct gcgtaacttc tttgaggaag atttgcagat tcgcttccgt    5100
ccttcctact tcccgtttac cgaaccttct gcagaagtgg acgtcatggg taaaaacggt    5160
aaaatggctg aagtgctggg ctgcgggatg gtgcatccga acgtgttgcg taacgttggc    5220
atcgacccgg aagtttactc tggtttcggc ttcgggatgg ggatggagcg tctgactatg    5280
ttgcgttacg gcgtcaccga cctgcgttca ttcttcgaaa acgatctgcg tttcctcaaa    5340
cagtttaaat aaggtcttct ggttatcgaa ggtaaggtct ggcgaacggt gtattaccgg    5400
tttgctacca gggaagaacg ggaaggaaag atgagcacga acctggtttt taaggagtgt    5460
cgccagagtg ccgcgatgaa cgggtattg gcggtatatg gagttaaaag atgaccatct    5520
acattactga gctaataaca ggcctgctgg taatcgcagg cctttttatt tgggggagag    5580
ggaagtcatg aaaaaactaa cctttgaaat tcgatctcca gcacatcagc aaaacgctat    5640
tcacgcagta cagcaaatcc ttccagaccc aaccaaacca atcgtagtaa ccattcagga    5700
acgcaaccgc agcattataa aaattgcctg atacgctgcg cttatcaggc ctacaagttc    5760
agcgatctac attagccgca tccggcatga acaaagcgca ggaacaagcg tcgcatcatg    5820
cctctttgac ccacagctgc ggaaaacgta ctggtgcaaa acgcagggtt atgatcatca    5880
gcccaacgac gcacagcgca tgaaatgccc agtccatcag gtaattgccg ctgatactac    5940
gcagcacgcc agaaaaccac ggggcaagcc cggcgatgat aaaaccgatt ccctgcataa    6000
acgccaccag cttgccagca atagccggtt gcacagagtg atcgagcgcc agcagcaaac    6060
agagcggaaa cgcgccgccc agacctaacc cacacaccat cgcccacaat accggcaatt    6120
gcatcggcag ccagataaag ccgcagaacc ccaccagttg taacaccagc gccagcatta    6180
acagtttgcg ccgatcctga tggcgagcca tagcaggcat cagcaaagct cctgcggctt    6240
gcccaagcgt catcaatgcc agtaaggaac cgctgtactg cgcgctggca ccaatctcaa    6300
tatagaaagc gggtaaccag gcaatcaggc tggcgtaacc gccgttaatc agaccgaagt    6360
aaacacccag cgtccacgcg cggggagtga ataccacgcg aaccggagtg gttgttgtct    6420
tgtgggaaga ggcgaccctcg cgggcgcttt gccaccacca ggcaaagagc gcaacaacgg    6480
```

```
caggcagcgc ccaccaggcg agtgtttgat accaggtttc gctatgttga actaaccagg    6540
gcgttatggc ggcaccaagc ccaccgccgc ccatcagagc cgcggaccac agccccatca    6600
ccagtggcgt gcgctgctga aaccgccgtt taatcaccga aggcatcacc gcctgaatga    6660
tgccgatccc caccccacca agcagtgcgc tgctaagcag cagcgcactt tgcgggtaaa    6720
gctcacgcat caatgcaccg acggcaatca gaacagact gatggcgaca ctgcgacgtt     6780
cgctgacatg ctgatgaagc cagcttccgg ccagcgccag cccgcccatg gtaaccaccg    6840
gcagagcggt caacagggca gccacgctaa agctcattcc gctcgcctgg cgcaattgcg    6900
gtagcagtgg cccgacggag gtgagcagtg gtcgcatatt aagaccaatc agcaccagta    6960
ccagcagcat                                                            6970
```

<210> SEQ ID NO 3
<211> LENGTH: 1044
<212> TYPE: DNA
<213> ORGANISM: Artificial Sequence
<220> FEATURE:
<223> OTHER INFORMATION: synthetic construct; nucleotides 4309-5352 of
      SEQ ID NO:3

<400> SEQUENCE: 3

```
gtgcgtgttg actatttac ctctggcggt gataatggtt gcatgtacta aggaggttgt       60
atgtcacatc tcgcagaact ggttgccagt gcgaaggcgg ccattagcca ggcgtcagat     120
gttgccgcgt tagataatgt gcgcgtcgaa tatttgggta aaaagggca cttaaccctt      180 cagatgacga ccctgcgtga gctgccgcca gaagagcgtc cggcagctgg tgcggttatc     240
aacgaagcga aagagcaggt tcagcaggcg ctgaatgcgc gtaaagcgga actggaaagc    300
gctgcactga atgcgcgtct ggcggcggaa acgattgatg tctctctgcc aggtcgtcgc     360
attgaaaacg gcggtctgca tccggttacc cgtaccatcg accgtatcga agtttcttc     420 ggtgagcttg gctttaccgt ggcaaccggg ccggaaatcg aagacgatta tcataacttc    480
gatgctctga acattcctgg tcaccacccg gcgcgcgctg accacgacac tttctggttt     540
gacactaccc gcctgctgcg tacccagacc tctggcgtac agatccgcac catgaaagcc    600
cagcagccac cgattcgtat catcgcgcct ggccgtgttt atcgtaacga ctacgaccag    660
actcacacgc cgatgttcca tcagatggaa ggtctgattg ttgataccaa catcagcttt    720
accaacctga aaggcacgct gcacgacttc ctgcgtaact tcttgagga agatttgcag     780 attcgcttcc gtccttccta cttcccgttt accgaacctt ctgcagaagt ggacgtcatg    840
ggtaaaaacg gtaaatggct ggaagtgctg ggctgcggga tggtgcatcc gaacgtgttg    900
cgtaacgttg gcatcgaccc ggaagtttac tctggtttcg gcttcgggat ggggatggag    960
cgtctgacta tgttgcgtta cggcgtcacc gacctgcgtt cattcttcga aaacgatctg    1020
cgtttcctca aacagtttaa ataa                                           1044
```